US011235090B2

(12) United States Patent
David et al.

(10) Patent No.: US 11,235,090 B2
(45) Date of Patent: Feb. 1, 2022

(54) KITS AND METHODS FOR PREPARING PATHOGEN-INACTIVATED PLATELET COMPOSITIONS

(71) Applicant: Cerus Corporation, Concord, CA (US)

(72) Inventors: Tovo David, San Francisco, CA (US); Betsy Donnelly, Moraga, CA (US); Anna Erickson, Richmond, CA (US); Naheed Mufti, Danville, CA (US)

(73) Assignee: Cerus Corporation, Concord, CA (US)

( * ) Notice: Subject to any disclaimer, the term of this patent is extended or adjusted under 35 U.S.C. 154(b) by 93 days.

(21) Appl. No.: 15/910,836

(22) Filed: Mar. 2, 2018

(65) Prior Publication Data

US 2018/0289873 A1    Oct. 11, 2018

Related U.S. Application Data

(60) Provisional application No. 62/622,127, filed on Jan. 25, 2018, provisional application No. 62/467,021, filed on Mar. 3, 2017.

(51) Int. Cl.
A61K 35/19      (2015.01)
A61L 2/00       (2006.01)
A61M 1/02       (2006.01)
A61M 1/36       (2006.01)
A61M 1/34       (2006.01)

(52) U.S. Cl.
CPC ........... A61M 1/0272 (2013.01); A61K 35/19 (2013.01); A61L 2/0011 (2013.01); A61L 2/0029 (2013.01); A61L 2/0088 (2013.01); A61M 1/0209 (2013.01); A61M 1/3496 (2013.01); A61M 1/3679 (2013.01); A61M 1/3683 (2014.02); A61M 2202/0415 (2013.01); A61M 2202/0427 (2013.01)

(58) Field of Classification Search
None
See application file for complete search history.

(56) References Cited

U.S. PATENT DOCUMENTS

| | | |
|---|---|---|
| 5,167,656 A | 12/1992 | Lynn |
| 5,288,605 A | 2/1994 | Lin et al. |
| 5,399,719 A | 3/1995 | Wollowitz et al. |
| 5,459,030 A | 10/1995 | Lin et al. |
| 5,482,828 A | 1/1996 | Lin et al. |
| 5,559,250 A | 9/1996 | Cook |
| 5,578,736 A | 11/1996 | Wollowitz |
| 5,593,823 A | 1/1997 | Wollowitz et al. |
| 5,618,662 A | 4/1997 | Lin et al. |
| 5,625,079 A | 4/1997 | Wollowitz et al. |
| 5,691,132 A | 11/1997 | Wollowitz et al. |
| 5,908,742 A | 6/1999 | Lin et al. |
| 5,965,349 A | 10/1999 | Lin |
| 6,017,691 A | 1/2000 | Wollowitz et al. |
| 6,093,725 A | 7/2000 | Cook et al. |
| 6,099,734 A | 8/2000 | Mclarty |
| 6,133,460 A | 10/2000 | Wollowitz et al. |
| 6,143,490 A | 11/2000 | Cook et al. |
| 6,171,777 B1 | 1/2001 | Cook |
| 6,177,441 B1 | 1/2001 | Cook et al. |
| 6,194,139 B1 | 2/2001 | Wollowitz |
| 6,270,952 B1 | 8/2001 | Cook et al. |
| 6,281,225 B1 | 8/2001 | Hearst et al. |
| 6,364,864 B1 * | 4/2002 | Mohiuddin ............... A61J 1/10 206/219 |
| 6,410,219 B1 | 6/2002 | Cook et al. |
| 6,420,570 B1 | 7/2002 | Wollowitz |
| 6,433,343 B1 | 8/2002 | Cimino et al. |
| 6,455,286 B1 | 9/2002 | Wollowitz |
| 6,469,052 B2 | 10/2002 | Wollowitz |
| 6,503,699 B1 | 1/2003 | Wollowitz et al. |
| 6,514,987 B1 | 2/2003 | Cook et al. |
| 6,544,727 B1 | 4/2003 | Hei |
| 6,548,242 B2 | 4/2003 | Horowitz et al. |
| 6,565,802 B1 | 5/2003 | Hanley |
| 6,586,749 B2 | 7/2003 | Cimino |
| 6,686,480 B2 | 2/2004 | Wollowitz |
| 6,709,810 B2 | 3/2004 | Cook |
| 6,936,413 B1 | 8/2005 | Bischof |
| 6,949,753 B2 | 9/2005 | Cimino |
| 6,951,713 B2 | 10/2005 | Hei et al. |
| 7,025,877 B1 | 4/2006 | De Gheldere et al. |
| 7,037,642 B2 | 5/2006 | Hei |
| 7,068,361 B2 | 6/2006 | Cimino |
| 7,264,608 B2 | 9/2007 | Bischof |
| 7,293,985 B2 | 11/2007 | Cook |
| 7,445,756 B2 | 11/2008 | Moore |

(Continued)

FOREIGN PATENT DOCUMENTS

WO  WO-1993/00005 A1   1/1993
WO  WO-1993/17553 A1   9/1993

(Continued)

OTHER PUBLICATIONS

Abonnenc, M. et al. (Apr. 15, 2015). "In vitro Study of Platelet Function Confirms the Contribution of the Ultraviolet B (UVB) Radiation in the Lesions Observed in Riboflavin/UVB-Treated Platelet Concentrates," Transfusion 55(9):2219-2230.

Erickson, A. et al. (Apr. 2017). "Plasma Treated With Amotosalen and Ultraviolet A Light Retains Activity for Hemostasis After 5 Days Post-Thaw Storage at 1 to 6 Degree C," Transfusion 57(4):997-1006.

FDA: (Mar. 10, 2016). "INTERCEPT Blood System for Platelets—Dual Storage (DS) Processing Set," retrieved from URL:https://www.fda.gov/downloads/BiologicsBloodVaccines/BloodBloodProducts/ApprovedProducts/PremarketApprovalsPMAs/UCM427522.pdf, last visited Jun. 7, 2018.

(Continued)

Primary Examiner — Emily A Cordas
(74) Attorney, Agent, or Firm — Morrison & Foerster LLP

(57) ABSTRACT

Provided are methods for preparing pathogen-inactivated platelet compositions, as well as processing sets and compositions related thereto.

29 Claims, 4 Drawing Sheets

(56) References Cited

U.S. PATENT DOCUMENTS

| | | | |
|---|---|---|---|
| 7,534,348 B2 | 5/2009 | Reitz | |
| 7,611,831 B2 | 11/2009 | Hei | |
| 7,655,392 B2 | 2/2010 | Stassinopoulos | |
| 8,296,071 B2 | 10/2012 | Edrich et al. | |
| 8,900,805 B2 | 12/2014 | Mufti | |
| 9,259,525 B2 | 2/2016 | Hei | |
| 9,713,627 B2 | 7/2017 | Mufti | |
| 10,357,516 B2 | 7/2019 | Mufti | |
| 10,799,533 B2 | 10/2020 | Corash | |
| 10,842,818 B2 | 11/2020 | Vermeij | |
| 2001/0009756 A1 | 7/2001 | Hei | |
| 2001/0018179 A1 | 8/2001 | Hei | |
| 2002/0006393 A1 | 1/2002 | Wollowitz | |
| 2002/0028432 A1 | 3/2002 | Cook | |
| 2002/0042043 A1 | 4/2002 | Stassinopoulos | |
| 2002/0115585 A1 | 8/2002 | Hei | |
| 2002/0182581 A1 | 12/2002 | Cook | |
| 2002/0192632 A1 | 12/2002 | Hei et al. | |
| 2003/0062483 A1 | 4/2003 | Cimino | |
| 2003/0105339 A1 | 6/2003 | Wollowitz | |
| 2003/0113704 A1 | 6/2003 | Stassinopoulos | |
| 2003/0207247 A1 | 11/2003 | Stassinopoulos | |
| 2004/0021809 A1 | 2/2004 | Sumiyoshi et al. | |
| 2004/0029897 A1 | 2/2004 | Cook | |
| 2004/0180321 A1 | 9/2004 | Cook | |
| 2004/0185544 A9 | 9/2004 | Hei | |
| 2004/0185553 A9 | 9/2004 | Hei | |
| 2004/0197343 A1 | 10/2004 | Dubensky et al. | |
| 2004/0228877 A1 | 11/2004 | Dubensky et al. | |
| 2005/0142542 A1 | 6/2005 | Hei | |
| 2005/0175625 A1 | 8/2005 | Jaffee et al. | |
| 2005/0202395 A1 | 9/2005 | Edrich | |
| 2005/0249748 A1 | 11/2005 | Dubensky et al. | |
| 2005/0281783 A1 | 12/2005 | Kinch et al. | |
| 2006/0009399 A1 | 1/2006 | Davis | |
| 2006/0115466 A1 | 6/2006 | Stassinopoulos | |
| 2007/0031457 A1 | 2/2007 | Dubensky et al. | |
| 2007/0190029 A1 | 8/2007 | Pardoll et al. | |
| 2007/0190063 A1 | 8/2007 | Bahjat et al. | |
| 2007/0207170 A1 | 9/2007 | Dubensky et al. | |
| 2007/0207171 A1 | 9/2007 | Dubensky et al. | |
| 2010/0133160 A1 | 6/2010 | Hei | |
| 2011/0286987 A1 | 11/2011 | Mufti | |
| 2013/0143198 A1 | 6/2013 | Sailliol | |
| 2015/0056604 A1* | 2/2015 | Sehgal | A01N 1/0215 435/2 |
| 2015/0157665 A1 | 6/2015 | Mufti | |
| 2016/0354533 A1 | 12/2016 | Hei | |
| 2017/0027986 A1 | 2/2017 | Corash et al. | |
| 2017/0202882 A1 | 7/2017 | Vermeij | |
| 2017/0304363 A1 | 10/2017 | Corash | |
| 2018/0008639 A1 | 1/2018 | Mufti | |
| 2018/0185484 A1 | 7/2018 | Greenman | |
| 2018/0318348 A1 | 11/2018 | Corash | |
| 2019/0085289 A1 | 3/2019 | Greenman | |
| 2019/0209718 A1 | 7/2019 | Church | |
| 2019/0321407 A1 | 10/2019 | Erickson | |
| 2019/0369087 A1 | 12/2019 | North et al. | |
| 2020/0078406 A1 | 3/2020 | Weiner et al. | |
| 2020/0397935 A1 | 12/2020 | Church et al. | |
| 2020/0405891 A1 | 12/2020 | Church et al. | |
| 2021/0187020 A1 | 6/2021 | Corash et al. | |

FOREIGN PATENT DOCUMENTS

| | | |
|---|---|---|
| WO | WO-1994/03054 A1 | 2/1994 |
| WO | WO-1994/27433 A1 | 12/1994 |
| WO | WO-1995/00141 A1 | 1/1995 |
| WO | WO-1995/12973 A1 | 5/1995 |
| WO | WO-1995/19705 A1 | 7/1995 |
| WO | WO-1996/08965 A1 | 3/1996 |
| WO | WO-1996/14737 A1 | 5/1996 |
| WO | WO-1996/14739 A1 | 5/1996 |
| WO | WO-1996/14740 A1 | 5/1996 |
| WO | WO-1996/39815 A1 | 12/1996 |
| WO | WO-1996/39818 A1 | 12/1996 |
| WO | WO-1996/39820 A1 | 12/1996 |
| WO | WO-1996/40857 A1 | 12/1996 |
| WO | WO-1997/21346 A1 | 6/1997 |
| WO | WO-1998/18908 A1 | 5/1998 |
| WO | WO-1998/30327 A1 | 7/1998 |
| WO | WO199830545 A1 | 7/1998 |
| WO | WO-1999/03976 A2 | 1/1999 |
| WO | WO-1999/03976 A3 | 1/1999 |
| WO | WO199903976 A2 | 1/1999 |
| WO | WO199903976 A3 | 1/1999 |
| WO | WO-1999/26476 A1 | 6/1999 |
| WO | WO199926476 A1 | 6/1999 |
| WO | WO-1999/34839 A1 | 7/1999 |
| WO | WO-1999/34914 A1 | 7/1999 |
| WO | WO-1999/34915 A1 | 7/1999 |
| WO | WO199934839 A1 | 7/1999 |
| WO | WO-1999/63981 A2 | 12/1999 |
| WO | WO-1999/63981 A3 | 12/1999 |
| WO | WO-2001/91775 A2 | 12/2001 |
| WO | WO-2001/91775 A3 | 12/2001 |
| WO | WO-2003/47650 A2 | 6/2003 |
| WO | WO-2003/47650 A3 | 6/2003 |
| WO | WO-2003/049784 A2 | 6/2003 |
| WO | WO-2003/049784 A3 | 6/2003 |
| WO | WO-2003/061379 A2 | 7/2003 |
| WO | WO-2003/061379 A3 | 7/2003 |
| WO | WO-2003/065787 A2 | 8/2003 |
| WO | WO-2003/065787 A3 | 8/2003 |
| WO | WO-2003/078023 A1 | 9/2003 |
| WO | WO-2003/090794 A1 | 11/2003 |
| WO | WO-2004/049914 A2 | 6/2004 |
| WO | WO-2004/049914 A3 | 6/2004 |
| WO | WO-2004/050029 A2 | 6/2004 |
| WO | WO-2004/050029 A3 | 6/2004 |
| WO | WO-2004/050848 A2 | 6/2004 |
| WO | WO-2004/050848 A3 | 6/2004 |
| WO | WO-2004/050897 A2 | 6/2004 |
| WO | WO-2004/050897 A3 | 6/2004 |
| WO | WO2004084936 A2 | 10/2004 |
| WO | WO2004110481 A2 | 12/2004 |
| WO | WO2005009463 A2 | 2/2005 |
| WO | WO2004110481 A3 | 3/2005 |
| WO | WO2005037233 A2 | 4/2005 |
| WO | WO2005037233 A3 | 4/2005 |
| WO | WO2004084936 A3 | 6/2005 |
| WO | WO2005009463 A3 | 6/2005 |
| WO | WO-2005/067460 A2 | 7/2005 |
| WO | WO-2005/067460 A3 | 7/2005 |
| WO | WO2005071088 A2 | 8/2005 |
| WO | WO2005071088 A3 | 8/2005 |
| WO | WO2005092372 A2 | 10/2005 |
| WO | WO2005092372 A3 | 10/2005 |
| WO | WO-2006/050328 A1 | 5/2006 |
| WO | WO2007022511 A2 | 2/2007 |
| WO | WO2007022511 A3 | 2/2007 |
| WO | WO2007022520 A2 | 2/2007 |
| WO | WO2007022520 A3 | 2/2007 |
| WO | WO-2007/103261 A2 | 9/2007 |
| WO | WO-2007/103261 A3 | 9/2007 |
| WO | WO2007103225 A2 | 9/2007 |
| WO | WO2007103225 A3 | 9/2007 |
| WO | WO2007117371 A2 | 10/2007 |
| WO | WO2007117371 A3 | 10/2007 |
| WO | WO2009126786 A2 | 10/2009 |
| WO | WO2009126786 A3 | 7/2010 |
| WO | WO-2012/018484 A2 | 2/2012 |
| WO | WO-2012/018484 A3 | 2/2012 |
| WO | WO-2012/071135 A2 | 5/2012 |
| WO | WO-2012/071135 A3 | 5/2012 |
| WO | WO2016014854 A1 | 1/2016 |
| WO | WO2016057965 A1 | 4/2016 |
| WO | WO2016115535 A1 | 7/2016 |
| WO | WO2016210374 A1 | 12/2016 |
| WO | WO2017070619 A1 | 4/2017 |
| WO | WO-2017/120545 A2 | 7/2017 |
| WO | WO-2017/120545 A3 | 7/2017 |
| WO | WO2018119462 A1 | 6/2018 |

(56) References Cited

FOREIGN PATENT DOCUMENTS

| WO | WO2018125994 | A1 | 7/2018 |
|---|---|---|---|
| WO | WO2018161020 | A1 | 9/2018 |
| WO | WO2019060610 | A1 | 3/2019 |
| WO | WO2019133929 | A1 | 7/2019 |
| WO | 2020061537 | A1 | 3/2020 |
| WO | 2020263745 | A1 | 12/2020 |
| WO | 2020263759 | A2 | 12/2020 |
| WO | 2020264421 | A1 | 12/2020 |
| WO | 2020263759 | A3 | 1/2021 |

OTHER PUBLICATIONS

FDA: (Mar. 10, 2016). "INTERCEPT Blood System for Platelets—Small Volume (SV) Processing Set," retrieved from URL: https://www.fda.gov/downloads/BiologicsBloodVaccines/BloodBloodProducts/ApprovedProducts/PremarketApprovalsPMAs/UCM427512.pdf, last visited Jun. 7, 2018.

FDA: (Mar. 10, 2016). "INTERCEPT Blood System for Platelets—Large Volume (LV) Processing Set," retrieved from URL:https://www.fda.gov/downloads/BiologicsBloodVaccines/BloodBloodProducts/ApprovedProducts/PremarketApprovalsPMAs/UCM427525.pdf last visited Jun. 7, 2018.

International Search Report and Written Opinion, dated Jun. 22, 2018, for PCT Application No. PCT/US2018/020745, filed Mar. 2, 2018, 15 pages.

Irsch, J. et al. (2011, e-pub. Jan. 27, 2011). "Pathogen Inactivation of Platelet and Plasma Blood Components for Transfusion Using the INTERCEPT Blood System™," Transfus. Med. Hemother. 38:19-31.

International Preliminary Report on Patentability, dated Sep. 3, 2019, for PCT Application No. PCT/US2018/020745, filed Mar. 2, 2018, 7 pages.

Prodouz, K.N. et al. (Jan. 1992). "Effects of Two Viral Inactivation Methods on Platelets: Laser-UV Radiation and Merocyanine 540-Mediated Photoinactivation," *Blood Cells* 18(1):101-116.

Sofer, G. (Aug. 2002). "Virus Inactivation in the 1990s—and Into the 21st Century: Part 2, Red Blood Cells and Platelets," *BioPharm*. pp. 42-49.

U.S. Appl. No. 09/238,355, Greenman, W. et al, filed Jan. 27, 1999. (Not submitted herewith pursuant to the waiver of 37 C.F.R. § 1.98(a)(2)(iii) issued by the Office on Sep. 21, 2004.).

U.S. Appl. No. 15/543,159, Greenman, W et al, filed Jan. 15, 2016. (Not submitted herewith pursuant to the waiver of 37 C.F.R. § 1.98(a)(2)(iii) issued by the Office on Sep. 21, 2004.).

U.S. Appl. No. 15/770,186, Corash et al, filed Oct. 21, 2016. (Not submitted herewith pursuant to the waiver of 37 C.F.R. § 1.98(a)(2)(iii) issued by the Office on Sep. 21, 2004.).

U.S. Appl. No. 17/102,269, Vermeij, J. et al., filed Nov. 23, 2020. (Not submitted herewith pursuant to the waiver of 37 C.F.R. § 1.98(a)(2)(iil) issued by the Office on Sep. 21, 2004.).

U.S. Appl. No. 17/205,932, Corash L. et al, filed Mar. 18, 2021. (Not submitted herewith pursuant to the waiver of 37 C.F.R. § 1.98(a)(2)(iil) issued by the Office on Sep. 21, 2004.).

U.S. Appl. No. 17/277,680, Cahyadi, H.. et al, filed Mar. 18, 2021. (Not submitted herewith pursuant to the waiver of 37 C.F.R. § 1.98(a)(2)(iil) issued by the Office on Sep. 21, 2004.).

Intercept Blood System (Feb. 28, 2020). "Intercept Platelet Processing Set With Triple Storage Containers," 27 pages.

Intercept Blood System (May 26, 2020). "Intercept Platelet Processing Set With Dual Storage Containers," 27 pages.

\* cited by examiner

KITS AND METHODS FOR PREPARING PATHOGEN-INACTIVATED PLATELET COMPOSITIONS

CROSS REFERENCE TO RELATED APPLICATIONS

This application claims the priority benefit of U.S. Provisional Application Ser. No. 62/467,021, filed Mar. 3, 2017, and 62/622,127, filed Jan. 25, 2018, each of which is hereby incorporated by reference in its entirety.

TECHNICAL FIELD

The present disclosure relates to improved methods, compositions, and processing sets for preparing pathogen-inactivated platelet compositions.

BACKGROUND

Platelets are a blood component that plays a key role in hemostasis, clot stability and retraction, as well as in vascular repair and anti-microbial host defense. Thrombocytopenia, or low blood platelet count, can result from a number of conditions that, depending on severity, may require the transfusion of donor platelets for therapeutic treatment. Platelet transfusions are also administered prophylactically to reduce the risk for bleeding in patients with therapy-induced hypoproliferative thrombocytopenia, such as in patients receiving chemotherapy or stem cell transplant (e.g., hematopoietic progenitor cell transplant).

A variety of methods are used to collect and store platelet products for clinical use. Collections from donated whole blood are generally in the form of platelet concentrates (PCs) obtained using buffy coat or platelet rich plasma processing methods, and such PCs may be pooled (e.g., 4-6 individual donors) to generate a platelet unit of sufficient therapeutic dosage to meet per unit dosage criteria defined by governmental, regulatory, institution or accrediting organization standards. Apheresis collection provides a means to obtain platelet units of sufficient therapeutic dosage from a single donor, without the need for pooling, by utilizing automated cell separation systems that separate platelets from the donor blood and return remaining blood components to the donor during the donation process. Platelet products are typically suspended in plasma or a mixture of plasma and a synthetic storage media (e.g., platelet additive solution) prior to storage.

Regulatory criteria define certain quality measures for platelet products, as well as maximum storage duration between production of platelet units and clinical infusion into patients. Requirements for different parameters can vary among countries, including for example, minimum amounts of platelets per unit (e.g., platelet dose, therapeutic dosage unit, platelets per container) and minimum pH levels through the storage period (e.g., 5 days, 7 days). The current U.S. FDA requirement for pH is 95% confidence that 95% of components exhibit a pH 22° C. $\geq$6.2. In CE mark regions, the pH requirement is pH>6.4, but statistical requirements may vary from country to country. Maximum storage periods generally range from a few days up to 7 days, and reflect not only platelet quality parameters, but also risk of transfusion-transmitted infection which may increase over time with room temperature storage. Bacterial contamination of platelet components is the second most common cause of transfusion-related deaths in the U.S.

Options to mitigate the risk of transfusion-transmitted infection from platelet components include bacterial detection testing and use of pathogen inactivation technologies. Photochemical treatment with psoralens (e.g., amotosalen) and ultraviolet light (e.g, UVA) provides a means of pathogen inactivation against a broad spectrum of pathogens, including bacteria, viruses and parasites. The commercially available INTERCEPT® Blood System (Cerus Corp.) for photochemical pathogen inactivation of platelets is comprised of processing sets containing the photoactive psoralen compound amotosalen and a separate ultraviolet light illumination device. The processing sets further comprise a compound adsorption device for reducing the levels of residual amotosalen and free photoproducts in pathogen inactivated platelet preparations after illumination.

Although the current INTERCEPT® System is highly efficacious at mitigating the risk of transfusion-transmitted infection from platelet components, modifications to the system could lead to further improvements in platelet quality and storage duration, particularly for processing larger amounts and/or volumes of platelets, including larger amounts and/or volumes of platelets suspended in plasma.

SUMMARY

To meet this and other needs, the methods, compositions and processing sets described herein are useful, inter alia, for maintaining platelet quality during storage after pathogen inactivation, particularly when processing larger amounts and/or volumes of platelets, including platelets prepared in plasma.

In one aspect, the present disclosure provides a method of preparing a pathogen-inactivated platelet composition, comprising: (a) mixing a platelet composition with a pathogen inactivation compound (PIC); (b) photochemically inactivating the platelet composition in admixture with the PIC; and (c) transferring the resultant mixture of step (b) under sterile conditions to a container containing a compound adsorption device (CAD) to produce a pathogen-inactivated platelet composition; wherein at least one of (i) and (ii) applies: (i) the volume of the container containing the CAD is greater than 1.0 L; and (ii) the surface area of the interior of the container containing the CAD is greater than about 750 cm$^2$. In some embodiments, the method further comprises: (d) transferring the pathogen-inactivated platelet composition under sterile conditions from the container containing the CAD to one or more storage containers. In some embodiments, the one or more storage containers is one storage container. In some embodiments, the one or more storage containers is two storage containers. In some embodiments, the one or more storage containers is three storage containers. In some embodiments, the volume of the container containing the CAD is greater than 1.0 L. In some embodiments, the volume of the container containing the CAD is greater than 1.1 L. In some embodiments, the volume of the container containing the CAD is greater than about 1.2 L. In some embodiments, the volume of the container containing the CAD is about 1.3 L. In some embodiments, the volume of the container containing the CAD is about 1.5 L. In some embodiments, the volume of the container containing the CAD is less than about 1.6 L. In some embodiments, the volume of the container containing the CAD is about 1.2 L to about 1.6 L. In some embodiments, the surface area of the interior of the container containing the CAD is greater than about 750 cm$^2$. In some embodiments, the surface area of the interior of the container containing the CAD is greater than about 800 cm$^2$. In some embodiments, the surface area of the interior of the container containing the CAD is greater than about 850 cm$^2$. In some embodiments, the surface area of the interior of the container containing the CAD is about 900 cm$^2$. In some embodiments, the surface area of the interior of the container containing the CAD is less than about 1100 cm$^2$. In some embodiments, the surface area of the interior of the container containing the CAD is about 850 cm$^2$ to about 1100 cm$^2$. In some embodiments, the platelet composition comprises at least about $6.0 \times 10^{11}$ platelets. In some embodiments, the platelet composition comprises at least about $7.0 \times 10^{11}$ platelets. In some embodiments, the platelet composition comprises at least about $8.0 \times 10^{11}$ platelets. In some embodiments, the platelet composition comprises at least about $11.0 \times 10^{11}$ platelets. In some embodiments, the platelet composition comprises less than about $12.0 \times 10^{11}$ platelets. In some embodiments, the platelet composition comprises about $6.0 \times 10^{11}$ to about $12.0 \times 10^{11}$ platelets. In some embodiments, the platelet composition has a volume of at least about 350 mL. In some embodiments, the platelet composition has a volume of at least about 400 mL. In some embodiments, the platelet composition has a volume of at least about 450 mL. In some embodiments, the platelet composition has a volume of at least about 500 mL. In some embodiments, the platelet composition has a volume of at least about 600 mL. In some embodiments, the platelet composition has a volume of less than about 650 mL. In some embodiments, the platelet composition has a volume of about 350 mL to about 650 mL. In some embodiments, the platelet composition comprises plasma. In some embodiments, the platelet composition does not comprise platelet additive solution. In some embodiments, the platelet composition comprises platelet additive solution. In some embodiments, the platelet composition comprises about 53% to about 68% platelet additive solution. In some embodiments, the platelet composition comprises platelets suspended in a suspension medium consisting essentially of plasma. In some embodiments, the method comprises, prior to step (a), collecting one or more platelet donations from one or more donors. In some embodiments, the platelet composition is prepared from an apheresis donation. In some embodiments, the platelet composition is prepared from a whole blood donation. In some embodiments, the platelet composition comprises one platelet donation. In some embodiments, the platelet composition comprises two platelet donations. In some embodiments, the platelet composition comprises three or more platelet donations. In some embodiments, the CAD comprises at least about three grams of adsorbent beads. In some embodiments, the CAD comprises less than about seven grams of adsorbent beads. In some embodiments, the CAD comprises at least about seven grams of adsorbent beads. In some embodiments, the method comprises, prior to step (a), sterilely connecting a container containing the platelet composition to a container containing the PIC. In some embodiments, the method further comprises: after step (d), storing the pathogen-inactivated platelet composition in the one or more storage containers for at least 5 days at room temperature. In some embodiments, the storage is for at least 6 days at room temperature. In some embodiments, the storage is for at least 7 days at room temperature. In some embodiments, the storage is for up to 7 days at room temperature. In some embodiments, the pH (e.g., pH$_{22° C.}$) of the pathogen-inactivated platelet composition after storage is ≥6.2. In some embodiments, the pH (e.g., pH$_{22° C.}$) of the pathogen-inactivated platelet composition after storage is ≥6.4. In some embodiments, after step (c) and before step (d), the pathogen-inactivated platelet composition is stored in the container containing the CAD for between about 4 and about 24 hours. In some embodiments, the pathogen-inactivated platelet composition is one or more pathogen-inactivated platelet units suitable for infusion. In some embodiments, the pathogen-inactivated platelet composition is one pathogen-inactivated platelet unit suitable for infusion. In some embodiments, the pathogen-inactivated platelet composition is two pathogen-inactivated platelet units suitable for infusion. In some embodiments, the pathogen-inactivated platelet composition is three pathogen-inactivated platelet units suitable for infusion. In some embodiments, the pathogen-inactivated platelet unit suitable for infusion is a therapeutic dosage unit of pathogen-inactivated platelets. In some embodiments, the pathogen-inactivated platelet composition comprises at least $2.0 \times 10^{11}$ platelets. In some embodiments, the pathogen-inactivated platelet composition comprises at least $2.4 \times 10^{11}$ platelets. In some embodiments, the pathogen-inactivated platelet composition comprises at least $3.0 \times 10^{11}$ platelets.

In one aspect, the present disclosure provides a pathogen-inactivated platelet composition prepared by the method according to any of the above embodiments. In some embodiments, the pathogen-inactivated platelet composition is one or more pathogen-inactivated platelet units suitable for infusion. In some embodiments, the pathogen-inactivated platelet composition is one pathogen-inactivated platelet unit suitable for infusion. In some embodiments, the pathogen-inactivated platelet composition is two pathogen-inactivated platelet units suitable for infusion. In some embodiments, the pathogen-inactivated platelet composition is three pathogen-inactivated platelet units suitable for infusion. In some embodiments, the pathogen-inactivated platelet unit suitable for infusion is a therapeutic dosage unit of pathogen-inactivated platelets. In some embodiments, the pathogen-inactivated platelet composition comprises at least $2.0 \times 10^{11}$ platelets. In some embodiments, the pathogen-inactivated platelet composition comprises at least $2.4 \times 10^{11}$ platelets. In some embodiments, the pathogen-inactivated platelet composition comprises at least $3.0 \times 10^{11}$ platelets.

In one aspect, the present disclosure provides a method of infusing a platelet composition into a subject in need thereof, the method comprising infusing into the subject a pathogen-inactivated platelet composition prepared by the method according to any of the above embodiments or a pathogen-inactivated platelet composition according to any of the above embodiments.

In one aspect, the present disclosure provides a processing set for preparing a pathogen-inactivated platelet composition, comprising: (a) a first container that contains a pathogen inactivation compound (PIC) and is suitable for combining a platelet composition with the PIC; (b) a second container, coupled to the first container, within which the platelet composition in admixture with the PIC can be photochemically inactivated; and (c) a third container containing a compound adsorption device (CAD), wherein the third container is coupled to the second container such that the photochemically inactivated platelet composition can be transferred from the second container to the third container under sterile conditions; wherein at least one of (i) and (ii) applies: (i) the volume of the third container is greater than 1.0 L; and (ii) the surface area of the interior of the third container is greater than about 750 cm$^2$. In some embodiments, the processing set further comprises one or more fourth containers, wherein the one or more fourth containers are coupled to the third container such that the photochemically inactivated platelet composition can be transferred from the third container to the one or more fourth containers under sterile conditions to provide the pathogen-inactivated platelet composition. In some embodiments, the processing set comprises one fourth container. In some embodiments, the processing set comprises two fourth containers. In some embodiments, the processing set comprises three fourth containers. In some embodiments, the volume of the third container is greater than 1.0 L. In some embodiments, the volume of the third container is greater than 1.1 L. In some embodiments, the volume of the third container is greater than about 1.2 L. In some embodiments, the volume of the third container is about 1.3 L. In some embodiments, the volume of the third container is about 1.5 L. In some embodiments, the volume of the third container is less than 1.6 L. In some embodiments, the volume of the third container is about 1.2 L to about 1.6 L. In some embodiments, the surface area of the interior of the third container is greater than about 750 cm$^2$. In some embodiments, the surface area of the interior of the third container is greater than about 800 cm$^2$. In some embodiments, the surface area of the interior of the third container is greater than about 850 cm$^2$. In some embodiments, the surface area of the interior of the container containing the CAD is about 900 cm$^2$. In some embodiments, the surface area of the interior of the third container is less than about 1100 cm$^2$. In some embodiments, the surface area of the interior of the container containing the CAD is about 850 cm$^2$ to about 1100 cm$^2$. In some embodiments, the platelet composition comprises at least about $6.0 \times 10^{11}$ platelets. In some embodiments, the platelet composition comprises at least about $7.0 \times 10^{11}$ platelets. In some embodiments, the platelet composition comprises at least about $8.0 \times 10^{11}$ platelets. In some embodiments, the platelet composition comprises at least about $11.0 \times 10^{11}$ platelets. In some embodiments, the platelet composition comprises less than about $12.0 \times 10^{11}$ platelets. In some embodiments, the platelet composition comprises about $6.0 \times 10^{11}$ to about $12.0 \times 10^{11}$ platelets. In some embodiments, the platelet composition has a volume of at least about 350 mL. In some embodiments, the platelet composition has a volume of at least about 400 mL. In some embodiments, the platelet composition has a volume of at least about 450 mL. In some embodiments, the platelet composition has a volume of at least about 500 mL. In some embodiments, the platelet composition has a volume of at least about 600 mL. In some embodiments, the platelet composition has a volume of less than about 650 mL. In some embodiments, the platelet composition has a volume of about 350 mL to about 650 mL. In some embodiments, the platelet composition comprises plasma. In some embodiments, the platelet composition does not comprise platelet additive solution. In some embodiments, the platelet composition comprises platelet additive solution. In some embodiments, the platelet composition comprises about 53% to about 68% platelet additive solution. In some embodiments, the platelet composition comprises platelets suspended in a suspension medium consisting essentially of plasma. In some embodiments, the platelet composition comprises one or more platelet donations from one or more donors. In some embodiments, the platelet composition is prepared from an apheresis donation. In some embodiments, the platelet composition is prepared from a whole blood donation. In some embodiments, the platelet composition comprises one platelet donation. In some embodiments, the platelet composition comprises two platelet donations. In some embodiments, the platelet composition comprises three or more platelet donations. In some embodiments, the CAD comprises at least about three grams of adsorbent beads. In some embodiments, the CAD comprises less than about seven grams of adsorbent beads. In some embodiments, the CAD comprises at least about seven grams of adsorbent beads. In some embodiments, the first container is suitable for sterile coupling to a container containing the platelet composition. In some embodiments, the one or more fourth containers are suitable for storing the pathogen-inactivated platelet composition for at least 5 days at room temperature. In some embodiments, the one or more fourth containers are suitable for storing the pathogen-inactivated platelet composition for at least 6 days at room temperature. In some embodiments, the one or more fourth containers are suitable for storing the pathogen-inactivated platelet composition for at least 7 days at room temperature. In some embodiments, the one or more fourth containers are suitable for storing the pathogen-inactivated platelet composition for up to 7 days at room temperature. In some embodiments, the pH (e.g., $pH_{22° C.}$) of the pathogen-inactivated platelet composition after storage is ≥6.2. In some embodiments, the pH (e.g., $pH_{22° C.}$) of the pathogen-inactivated platelet composition after storage is ≥6.4. In some embodiments, the third container is suitable for storing the pathogen-inactivated platelet composition for between about 4 and about 24 hours. In some embodiments, the pathogen-inactivated platelet composition is one or more pathogen-inactivated platelet units suitable for infusion. In some embodiments, the pathogen-inactivated platelet composition is one pathogen-inactivated platelet unit suitable for infusion. In some embodiments, the pathogen-inactivated platelet composition is two pathogen-inactivated platelet units suitable for infusion. In some embodiments, the pathogen-inactivated platelet composition is three pathogen-inactivated platelet units suitable for infusion. In some embodiments, the pathogen-inactivated platelet unit suitable for infusion is a therapeutic dosage unit of pathogen-inactivated platelets. In some embodiments, the pathogen-inactivated platelet composition comprises at least $2.0 \times 10^{11}$ platelets. In some embodiments, the pathogen-inactivated platelet composition comprises at least $2.4 \times 10^{11}$ platelets. In some embodiments, the pathogen-inactivated platelet composition comprises at least $3.0 \times 10^{11}$ platelets.

In one aspect, the present disclosure provides a kit comprising a processing set for preparing a pathogen-inactivated platelet composition and instructions for using the processing set to prepare the pathogen-inactivated platelet composition, wherein, the processing set comprises: (a) a first container that contains a pathogen inactivation compound (PIC) and is suitable for combining a platelet composition with the PIC; (b) a second container, coupled to the first container, within which the platelet composition in admixture with the PIC can be photochemically inactivated; and (c) a third container containing a compound adsorption device (CAD), wherein the third container is coupled to the second container such that the photochemically inactivated platelet composition can be transferred from the second container to the third container under sterile conditions; wherein at least one of (i) and (ii) applies: (i) the volume of the third container is greater than 1.0 L; and (ii) the surface area of the interior of the third container is greater than about 750 cm$^2$. In some embodiments, the processing set further comprises one or more fourth containers, wherein the one or more fourth containers are coupled to the third container such that the photochemically inactivated platelet composition can be transferred from the third container to the one or more fourth containers under sterile conditions to provide the pathogen-inactivated platelet composition. In some embodiments, the processing set comprises one fourth container. In some embodiments, the processing set comprises two fourth containers. In some embodiments, the processing set comprises three fourth containers. In some embodiments, the volume of the third container is greater than 1.0 L. In some embodiments, the volume of the third container is greater than 1.1 L. In some embodiments, the volume of the third container is greater than about 1.2 L. In some embodiments, the volume of the third container is about 1.3 L. In some embodiments, the volume of the third container is about 1.5 L. In some embodiments, the volume of the third container is less than about 1.6 L. In some embodiments, the volume of the third container is about 1.2 L to about 1.6 L. In some embodiments, the surface area of the interior of the third container is greater than about 750 cm$^2$. In some embodiments, the surface area of the interior of the third container is greater than about 800 cm$^2$. In some embodiments, the surface area of the interior of the third container is greater than about 850 cm$^2$. In some embodiments, the surface area of the interior of the container containing the CAD is about 900 cm$^2$. In some embodiments, the surface area of the interior of the third container is less than about 1100 cm$^2$. In some embodiments, the surface area of the interior of the container containing the CAD is about 850 cm$^2$ to about 1100 cm$^2$. In some embodiments, the instructions indicate that the processing set is suitable for processing a platelet composition that comprises at least about $6.0 \times 10^{11}$ platelets. In some embodiments, the instructions indicate that the processing set is suitable for processing a platelet composition that comprises at least about $7.0 \times 10^{11}$ platelets. In some embodiments, the instructions indicate that the processing set is suitable for processing a platelet composition that comprises at least about $8.0 \times 10^{11}$ platelets. In some embodiments, the instructions indicate that the processing set is suitable for processing a platelet composition that comprises at least about $11.0 \times 10^{11}$ platelets. In some embodiments, the instructions indicate that the processing set is suitable for processing a platelet composition that comprises less than about $12.0 \times 10^{11}$ platelets. In some embodiments, the instructions indicate that the processing set is suitable for processing a platelet composition that comprises about $6.0 \times 10^{11}$ to about $12.0 \times 10^{11}$ platelets. In some embodiments, the instructions indicate that the processing set is suitable for processing a platelet composition having a volume of at least about 350 mL. In some embodiments, the instructions indicate that the processing set is suitable for processing a platelet composition having a volume of at least about 400 mL. In some embodiments, the instructions indicate that the processing set is suitable for processing a platelet composition having a volume of at least about 450 mL. In some embodiments, the instructions indicate that the processing set is suitable for processing a platelet composition having a volume of at least about 500 mL. In some embodiments, the instructions indicate that the processing set is suitable for processing a platelet composition having a volume of at least about 600 mL. In some embodiments, the instructions indicate that the processing set is suitable for processing a platelet composition having a volume of less than about 650 mL. In some embodiments, the instructions indicate that the processing set is suitable for processing a platelet composition having a volume of a volume of about 350 mL to about 650 mL. In some embodiments, the platelet composition comprises plasma. In some embodiments, the platelet composition does not comprise platelet additive solution. In some embodiments, the platelet composition comprises platelet additive solution. In some embodiments, the platelet composition comprises about 53% to about 68% platelet additive solution. In some embodiments, the platelet composition comprises platelets suspended in a suspension medium consisting essentially of plasma. In some embodiments, the platelet composition comprises one or more platelet donations from one or more donors. In some embodiments, the platelet composition is prepared from an apheresis donation. In some embodiments, the platelet composition is prepared from a whole blood donation. In some embodiments, the platelet composition comprises one platelet donation. In some embodiments, the platelet composition comprises two platelet donations. In some embodiments, the platelet composition comprises three or more platelet donations. In some embodiments, the CAD comprises at least about three grams of adsorbent beads. In some embodiments, the CAD comprises less than about seven grams of adsorbent beads. In some embodiments, the CAD comprises at least about seven grams of adsorbent beads. In some embodiments, the first container is suitable for sterile coupling to a container containing the platelet composition. In some embodiments, the one or more fourth containers are suitable for storing the pathogen-inactivated platelet composition for at least 5 days at room temperature. In some embodiments, the one or more fourth containers are suitable for storing the pathogen-inactivated platelet composition for at least 6 days at room temperature. In some embodiments, the one or more fourth containers are suitable for storing the pathogen-inactivated platelet composition for at least 7 days at room temperature. In some embodiments, the one or more fourth containers are suitable for storing the pathogen-inactivated platelet composition for up to 7 days at room temperature. In some embodiments, the instructions indicate that the processing set (e.g., the one or more fourth containers) is suitable for storing the pathogen-inactivated platelet composition for at least 5 days at room temperature. In some embodiments, the instructions indicate that the processing set (e.g., the one or more fourth containers) is suitable for storing the pathogen-inactivated platelet composition for at least 6 days at room temperature. In some embodiments, the instructions indicate that the processing set (e.g., the one or more fourth containers) is suitable for storing the pathogen-inactivated platelet composition for at least 7 days at room temperature. In some embodiments, the instructions indicate that the processing set (e.g., the one or more fourth containers) is suitable for storing the pathogen-inactivated platelet composition for up to 7 days at room temperature. In some embodiments, the pH (e.g., pH$_{22° C.}$) of the pathogen-inactivated platelet composition after storage is ≥6.2. In some embodiments, the pH (e.g., pH$_{22° C.}$) of the pathogen-inactivated platelet composition after storage is ≥6.4. In some embodiments, the third container is suitable for storing the pathogen-inactivated platelet composition for between about 4 and about 24 hours.

It is to be understood that one, some, or all of the properties of the various embodiments described herein may be combined to form other embodiments. These and other aspects will become apparent to one of skill in the art. These and other embodiments are further described by the detailed description that follows.

DETAILED DESCRIPTION

Figure 1:
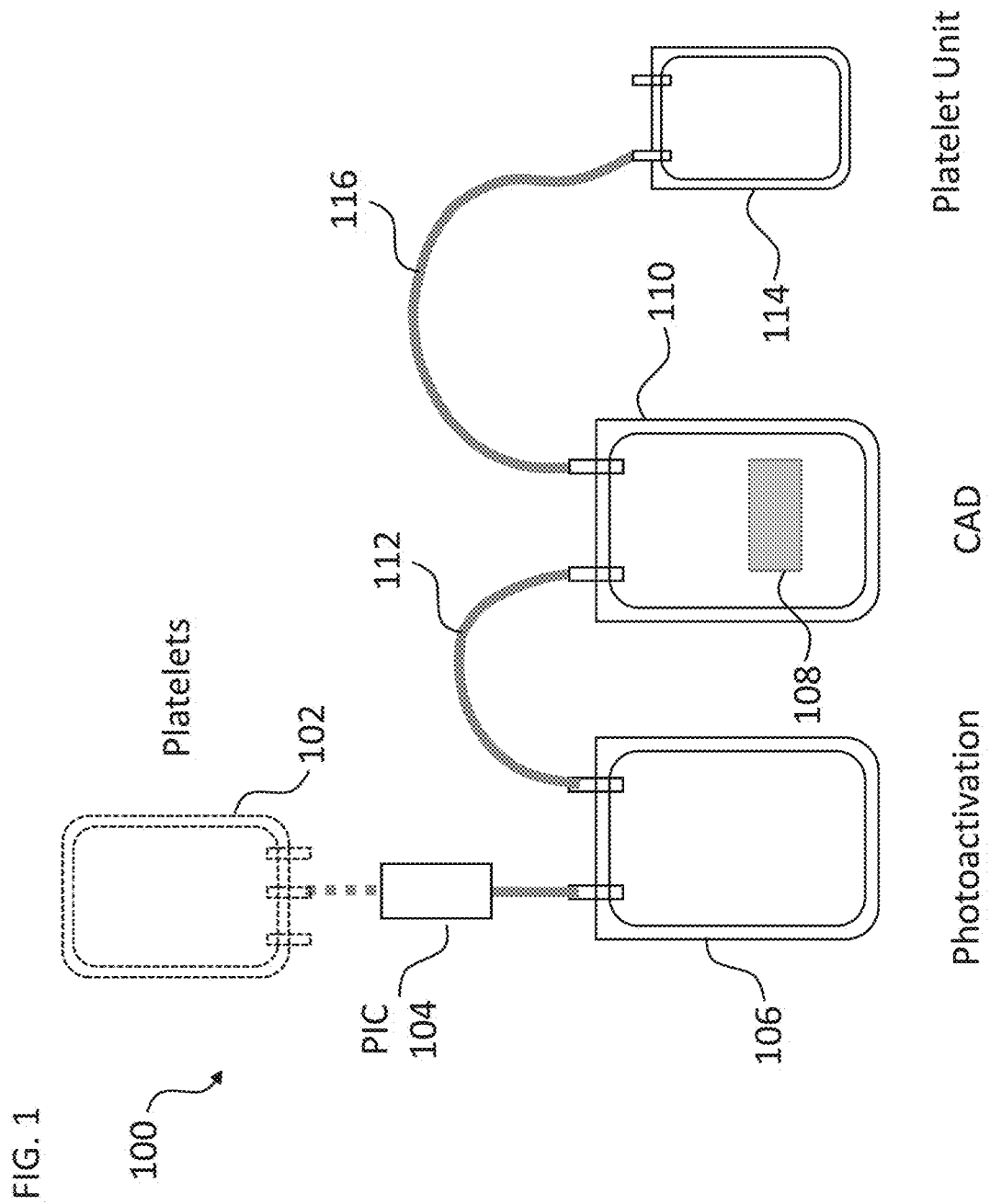
FIG. 1 shows an exemplary processing kit for use in preparing a pathogen inactivated platelet composition in accordance with some embodiments. Dotted components depict one container with platelets (e.g., donor platelets) sterilely connected to the processing kit. Abbreviations: PIC, pathogen inactivating compound; CAD, compound adsorption device. Drawing not to scale.

The term "pathogen inactivation process" means a process useful to inactivate pathogens that may be present in a preparation of platelets or other platelet composition, such as a platelet donation, where it is understood that the process does not necessarily inactivate completely all pathogens that may be present, but substantially reduces the amount of pathogens to significantly reduce the risk of a transfusion associated disease (e.g., transfusion transmitted infection, TTI). The inactivation of a pathogen may be assayed by measuring the number of infective pathogens (e.g., viral particles, bacteria) in a certain volume, before and after a pathogen inactivation process, and the level of inactivation is typically represented in the log reduction in the infectivity of the pathogen, or log reduction in titer. Methods of assaying log reduction in titer, and measurements thereof for pathogen inactivation are known in the art. When the inactivation process is tested against a variety of pathogens, the reduction in a particular active pathogen is at least about 1 log, at least about 2 log, at least about 3 log, at least about 4 log, or at least about 5 log reduction in titer. A variety of pathogen inactivation processes are known in the art and may be used in the methods of the present disclosure, including for example, commercially available pathogen inactivation processes, such as the INTERCEPT® Blood System (Cerus Corp). In certain embodiments, a pathogen inactivation process may comprise treating with a pathogen inactivating compound.

The term "pathogen inactivating compound" means any suitable compound, such as a small organic compound, that can be used to inactivate a pathogen that may be present in a platelet-containing blood product. A "photoactivated pathogen inactivation compound" is a suitable compound that requires some level of light (e.g., ultraviolet light) in order to sufficiently inactivate (e.g., photochemically inactivate) a pathogen. Such compounds are preferred in the inactivation of pathogens in platelet products as they provide control over the inactivation process. Such photoactivated pathogen inactivation compounds described herein include psoralens, isoalloxazines, alloxazines, phthalocyanines, phenothiazines, and porphyrins, where these terms are understood to encompass a general class of compounds, i.e. the core compound and suitable derivatives thereof. For example psoralens or a psoralen generally describes the psoralen core compound and any derivative thereof (e.g. amotosalen), isoalloxazines or an isoalloxazine generally describes the isoalloxazine core and any derivative thereof (e.g. riboflavin), and so forth. Such derivatives comprise the core compound structure as well as additional substituents on the core. Descriptions of such compounds include any salts thereof.

The term "amotosalen" means the compound 3-(2-aminoethoxymethyl)-2,5,9-trimethylfuro[3,2-g]chromen-7-one and any salts thereof. The compound may also be referred to as 4'-(4-amino-2-oxa)butyl-4,5',8-trimethyl psoralen. The compound may also be referred to as 3-[(2-aminoethoxy)methyl]-2.5.9-trimethyl-7H-furo [3, 2-g] [1] benzopyran-7-one. Where the inactivation of platelets includes adding amotosalen HCl (the HCl salt of amotosalen) to a platelet composition, the removal of this compound from the platelet composition is not limited to the removal of amotosalen HCl, as the amotosalen can be present in solution as other salts or as the free base. As used in the methods described herein, removal of amotosalen means removal of the compound in any form, e.g. as the free base or as any salt, as measured by the assays described herein.

The term "suitable for infusion" refers to a platelet composition (e.g., pathogen-inactivated platelet composition) able to be used for an infusion (e.g., a transfusion) into a subject (e.g., a human patient) according to medical judgement. In some embodiments, suitability refers to having sufficient biological activity for its intended use, i.e., for use where an infusion of human platelets is indicated, including, without limitation, prophylactic and therapeutic infusion, such as for example treatment of thrombocytopenia or to reduce the risk of bleeding in patients with potential for therapy-induced hypoproliferative thrombocytopenia. In some embodiments, suitability refers to having sufficient safety. In some embodiments, suitability refers to meeting one or more standards (e.g., having suitable characteristics, having a level of a biological activity or function, having at least a minimum platelet dose) established by an accrediting agency or regulatory body that governs infusion practices, such as the AABB.

Pathogen-Inactivated Platelet Compositions and Methods

Certain aspects of the present disclosure provide pathogen-inactivated platelet compositions and methods (e.g., methods of preparation) related thereto. A particular benefit, among others, provided by the improvements disclosed herein is the opportunity to produce pathogen-inactivated platelet compositions that retain favorable characteristics (in particular, suitable pH, but also including and not limited to any of dissolved oxygen, carbon dioxide, glucose, lactate, ATP, LDH, p-selectin expression (e.g., CD62P), cellular morphology (e.g., morphology score), extent of shape change or ESC, and hypotonic shock response or HSR) for a longer duration and/or at a level closer to untreated (e.g., non-pathogen-inactivated) platelet compositions during storage after undergoing pathogen inactivation (e.g., as described herein) than is provided with existing methods and processing sets. Such characteristics may be those known in the art and commonly measured, such as for example, using assays known in the art. It is a discovery of the present disclosure that the conditions under which a platelet composition, having undergone pathogen inactivation by photochemical treatment, is subjected to processing with a compound adsorption device, or CAD (e.g., stored with a CAD, incubated with a CAD), can significantly improve the characteristics (e.g., pH outcome) of a pathogen-inactivated platelet composition after storage, following the pathogen inactivation process. The improved characteristics are particularly useful for processing larger amounts (e.g., quantities) of platelets, including larger amounts of platelets suspended in higher concentrations of plasma (e.g., 100% plasma). The methods, compositions, and processing sets disclosed herein provide pathogen-inactivated platelet compositions with improved pH even after undergoing pathogen inactivation and storage (e.g., for up to 7 days).

In some embodiments, the methods of the present disclosure for preparing a pathogen-inactivated platelet composition include: (a) mixing a platelet composition with a pathogen inactivation compound (PIC); (b) photochemically inactivating the platelet composition in admixture with the PIC; and transferring the resultant mixture of step (b) under sterile conditions to a container containing a compound adsorption device (CAD) to produce a pathogen-inactivated platelet composition, wherein at least one of (i) and (ii) applies: (i) the volume of the container containing the CAD is greater than 1.0 L (e.g., about 1.2 L or greater); and (ii) the surface area of the interior of the container containing the CAD is greater than about 750 $cm^2$ (e.g., about 800 $cm^2$ or greater). Further provided herein are pathogen-inactivated platelet compositions produced by any of the methods of the present disclosure.

In some embodiments, the volume of a container containing a CAD of the present disclosure is greater than 1.0 liter (L), greater than about 1.1 L, greater than about 1.2 L, greater than about 1.3 L, greater than about 1.4 L, greater than about 1.5 L, or greater than about 1.6 L. In some embodiments, the volume of a container containing a CAD of the present disclosure is less than about any of the following volumes: 1.6 L, 1.5 L, 1.4 L, 1.3 L, or 1.2 L. In some embodiments, the volume of a container containing a CAD of the present disclosure is greater than about any of the following volumes: 1.1 L, 1.2 L, 1.3 L, 1.4 L, or 1.5 L. That is, the volume of a container containing a CAD of the present disclosure can be any volume within a range having an upper limit of 1.6 L, 1.5 L, 1.4 L, 1.3 L, or 1.2 L and an independently selected lower limit of 1.1 L, 1.2 L, 1.3 L, 1.4 L, or 1.5 L, wherein the upper limit is greater than the lower limit. In certain embodiments, the volume of a container containing a CAD of the present disclosure is about 1.1 L to about 1.6 L, about 1.1 L to about 1.5 L, about 1.1 L to about 1.4 L, about 1.1 L to about 1.3 L, about 1.1 L to about 1.2 L, about 1.2 L to about 1.6 L, about 1.2 L to about 1.5 L, about 1.2 L to about 1.4 L, about 1.2 L to about 1.3 L, about 1.3 L to about 1.6 L, about 1.3 L to about 1.5 L, about 1.3 L to about 1.4 L, about 1.4 L to about 1.6 L, about 1.4 L to about 1.5 L, or about 1.5 L to about 1.6 L. In some embodiments, the volume of a container containing a CAD of the present disclosure is about 1.1 L, about 1.2 L, about 1.3 L, about 1.4 L, about 1.5 L, or about 1.6 L.

In some embodiments, the surface area of the interior (e.g., inner surface area) of a container containing a CAD of the present disclosure is greater than about 750 $cm^2$, greater than about 800 $cm^2$, greater than about 850 $cm^2$, greater than about 900 $cm^2$, greater than about 950 $cm^2$, greater than about 1000 $cm^2$, greater than about 1050 $cm^2$, greater than about 1100 $cm^2$, greater than about 1150 $cm^2$, greater than about 1200 $cm^2$, or greater than about 1300 $cm^2$. In some embodiments, the surface area of the interior of a container containing a CAD of the present disclosure is less than about 1400 $cm^2$, less than about 1300 $cm^2$, less than about 1200 $cm^2$, less than about 1150 $cm^2$, less than about 1100 $cm^2$, less than about 1050 $cm^2$, less than about 1000 $cm^2$, less than about 950 $cm^2$, less than about 900 $cm^2$, less than about 850 $cm^2$, or less than about 800 $cm^2$. That is, the surface area of the interior of a container containing a CAD of the present disclosure can be an surface area within a range having an upper limit of 1400 $cm^2$, 1300 $cm^2$, 1200 $cm^2$, 1150 $cm^2$, 1100 $cm^2$, 1050 $cm^2$, 1000 $cm^2$, 950 $cm^2$, 900 $cm^2$, 850 $cm^2$, or 800 $cm^2$ and an independently selected lower limit of 750 $cm^2$, 800 $cm^2$, 850 $cm^2$, 900 $cm^2$, 950 $cm^2$, 1000 $cm^2$, 1050 $cm^2$, 1100 $cm^2$, 1150 $cm^2$, 1200 $cm^2$, or 1300 $cm^2$, wherein the upper limit is greater than the lower limit. In some embodiments, the surface area of the interior of a container containing a CAD of the present disclosure is about 750 $cm^2$, about 800 $cm^2$, about 850 $cm^2$, about 900 $cm^2$, about 950 $cm^2$, about 1000 $cm^2$, about 1050 $cm^2$, about 1100 $cm^2$, about 1150 $cm^2$, or about 1200 $cm^2$. In certain embodiments, the surface area of the interior of a container containing a CAD of the present disclosure is about 750 $cm^2$ to about 1400 $cm^2$, about 750 $cm^2$ to about 1300 $cm^2$, about 750 $cm^2$ to about 1200 $cm^2$, about 750 $cm^2$ to about 1150 $cm^2$, about 750 $cm^2$ to about 1100 $cm^2$, about 750 $cm^2$ to about 1050 $cm^2$, about 750 $cm^2$ to about 1000 $cm^2$, about 750 $cm^2$ to about 950 $cm^2$, about 750 $cm^2$ to about 900 $cm^2$, about 750 $cm^2$ to about 850 $cm^2$, about 750 $cm^2$ to about 800 $cm^2$, about 800 $cm^2$ to about 1400 $cm^2$, about 800 $cm^2$ to about 1300 $cm^2$, about 800 $cm^2$ to about 1200 $cm^2$, about 800 $cm^2$ to about 1150 $cm^2$, about 800 $cm^2$ to about 1100 $cm^2$, about 800 $cm^2$ to about 1050 $cm^2$, about 800 $cm^2$ to about 1000 $cm^2$, about 800 $cm^2$ to about 950 $cm^2$, about 800 $cm^2$ to about 900 $cm^2$, about 800 $cm^2$ to about 850 $cm^2$, about 850 $cm^2$ to about 1400 $cm^2$, about 850 $cm^2$ to about 1300 $cm^2$, about 850 $cm^2$ to about 1200 $cm^2$, about 850 $cm^2$ to about 1150 $cm^2$, about 850 $cm^2$ to about 1100 $cm^2$, about 850 $cm^2$ to about 1050 $cm^2$, about 850 $cm^2$ to about 1000 $cm^2$, about 850 $cm^2$ to about 950 $cm^2$, about 850 $cm^2$ to about 900 $cm^2$, about 900 $cm^2$ to about 1400 $cm^2$, about 900 $cm^2$ to about 1300 $cm^2$, about 900 $cm^2$ to about 1200 $cm^2$, about 900 $cm^2$ to about 1150 $cm^2$, about 900 $cm^2$ to about 1100 $cm^2$, about 900 $cm^2$ to about 1050 $cm^2$, about 900 $cm^2$ to about 1000 $cm^2$, about 900 $cm^2$ to about 950 $cm^2$, about 950 $cm^2$ to about 1400 $cm^2$, about 950 $cm^2$ to about 1300 $cm^2$, about 950 $cm^2$ to about 1200 $cm^2$, about 950 $cm^2$ to about 1150 $cm^2$, about 950 $cm^2$ to about 1100 $cm^2$, about 950 $cm^2$ to about 1050 $cm^2$, about 950 $cm^2$ to about 1000 $cm^2$, about 1000 $cm^2$ to about 1400 $cm^2$, about 1000 $cm^2$ to about 1300 $cm^2$, about 1000 $cm^2$ to about 1200 $cm^2$, about 1000 $cm^2$ to about 1150 $cm^2$, about 1000 $cm^2$ to about 1100 $cm^2$, about 1000 $cm^2$ to about 1050 $cm^2$, about 1050 $cm^2$ to about 1400 $cm^2$, about 1050 $cm^2$ to about 1300 $cm^2$, about 1050 $cm^2$ to about 1200 $cm^2$, about 1050 $cm^2$ to about 1150 $cm^2$, about 1050 $cm^2$ to about 1100 $cm^2$, about 1100 $cm^2$ to about 1400 $cm^2$, about 1100 $cm^2$ to about 1300 $cm^2$, about 1100 $cm^2$ to about 1200 $cm^2$, about 1200 $cm^2$ to about 1400 $cm^2$, about 1200 $cm^2$ to about 1300 $cm^2$, or about 1300 $cm^2$ to about 1400 $cm^2$.

In some embodiments, the volume of a container containing a CAD of the present disclosure is greater than 1.0 L and the surface area of the interior (e.g., inner surface area) of the container containing a CAD is greater than about 750 $cm^2$, greater than about 800 $cm^2$, greater than about 850 $cm^2$, greater than about 900 $cm^2$, greater than about 950 $cm^2$, greater than about 1000 $cm^2$, greater than about 1050 $cm^2$, greater than about 1100 $cm^2$, greater than about 1150 $cm^2$, greater than about 1200 $cm^2$, or greater than about 1300 $cm^2$. In some embodiments, the volume of a container containing a CAD of the present disclosure is greater than about 1.1 L and the surface area of the interior (e.g., inner surface area) of the container containing a CAD is greater than about 750 cm$^2$, greater than about 800 cm$^2$, greater than about 850 cm$^2$, greater than about 900 cm$^2$, greater than about 950 cm$^2$, greater than about 1000 cm$^2$, greater than about 1050 cm$^2$, greater than about 1100 cm$^2$, greater than about 1150 cm$^2$, greater than about 1200 cm$^2$, or greater than about 1300 cm$^2$. In some embodiments, the volume of a container containing a CAD of the present disclosure is greater than about 1.2 L and the surface area of the interior (e.g., inner surface area) of the container containing a CAD is greater than about 750 cm$^2$, greater than about 800 cm$^2$, greater than about 850 cm$^2$, greater than about 900 cm$^2$, greater than about 950 cm$^2$, greater than about 1000 cm$^2$, greater than about 1050 cm$^2$, greater than about 1100 cm$^2$, greater than about 1150 cm$^2$, greater than about 1200 cm$^2$, or greater than about 1300 cm$^2$. In some embodiments, the volume of a container containing a CAD of the present disclosure is greater than about 1.3 L and the surface area of the interior (e.g., inner surface area) of the container containing a CAD is greater than about 750 cm$^2$, greater than about 800 cm$^2$, greater than about 850 cm$^2$, greater than about 900 cm$^2$, greater than about 950 cm$^2$, greater than about 1000 cm$^2$, greater than about 1050 cm$^2$, greater than about 1100 cm$^2$, greater than about 1150 cm$^2$, greater than about 1200 cm$^2$, or greater than about 1300 cm$^2$. In some embodiments, the volume of a container containing a CAD of the present disclosure is greater than about 1.4 L and the surface area of the interior (e.g., inner surface area) of the container containing a CAD is greater than about 750 cm$^2$, greater than about 800 cm$^2$, greater than about 850 cm$^2$, greater than about 900 cm$^2$, greater than about 950 cm$^2$, greater than about 1000 cm$^2$, greater than about 1050 cm$^2$, greater than about 1100 cm$^2$, greater than about 1150 cm$^2$, greater than about 1200 cm$^2$, or greater than about 1300 cm$^2$. In some embodiments, the volume of a container containing a CAD of the present disclosure is greater than about 1.5 L and the surface area of the interior (e.g., inner surface area) of the container containing a CAD is greater than about 750 cm$^2$, greater than about 800 cm$^2$, greater than about 850 cm$^2$, greater than about 900 cm$^2$, greater than about 950 cm$^2$, greater than about 1000 cm$^2$, greater than about 1050 cm$^2$, greater than about 1100 cm$^2$, greater than about 1150 cm$^2$, greater than about 1200 cm$^2$, or greater than about 1300 cm$^2$. In some embodiments, the volume of a container containing a CAD of the present disclosure is greater than about 1.6 L and the surface area of the interior (e.g., inner surface area) of the container containing a CAD is greater than about 750 cm$^2$, greater than about 800 cm$^2$, greater than about 850 cm$^2$, greater than about 900 cm$^2$, greater than about 950 cm$^2$, greater than about 1000 cm$^2$, greater than about 1050 cm$^2$, greater than about 1100 cm$^2$, greater than about 1150 cm$^2$, greater than about 1200 cm$^2$, or greater than about 1300 cm$^2$. In some embodiments, the volume of the container containing a CAD is less than about any of the following volumes (in L): 1.6, 1.5, 1.4, 1.3, or 1.2. In some embodiments, the volume of the container containing a CAD is about 1.1 L, about 1.2 L, about 1.3 L, about 1.4 L, about 1.5 L, or about 1.6 L. In some embodiments, the surface area of the interior of the container containing a CAD is less than about 1400 cm$^2$, less than about 1300 cm$^2$, less than about 1200 cm$^2$, less than about 1150 cm$^2$, less than about 1100 cm$^2$, less than about 1050 cm$^2$, less than about 1000 cm$^2$, less than about 950 cm$^2$, less than about 900 cm$^2$, less than about 850 cm$^2$, or less than about 800 cm$^2$. In some embodiments, the surface area of the interior of the container containing a CAD is about 750 cm$^2$, about 800 cm$^2$, about 850 cm$^2$, about 900 cm$^2$, about 950 cm$^2$, about 1000 cm$^2$, about 1050 cm$^2$, about 1100 cm$^2$, about 1150 cm$^2$, or about 1200 cm$^2$.

In some embodiments, the volume of a container containing a CAD of the present disclosure is about 1.1 L to about 1.6 L, and the surface area of the interior of the container containing a CAD is about 750 cm$^2$ to about 1400 cm$^2$, about 800 cm$^2$ to about 1300 cm$^2$, about 800 cm$^2$ to about 1200 cm$^2$, about 850 cm$^2$ to about 1200 cm$^2$, about 850 cm$^2$ to about 1150 cm$^2$, or about 850 cm$^2$ to about 1100 cm$^2$. In some embodiments, the volume of a container containing a CAD of the present disclosure is about 1.2 L to about 1.6 L, and the surface area of the interior of the container containing a CAD is about 750 cm$^2$ to about 1400 cm$^2$, about 800 cm$^2$ to about 1300 cm$^2$, about 800 cm$^2$ to about 1200 cm$^2$, about 850 cm$^2$ to about 1200 cm$^2$, about 850 cm$^2$ to about 1150 cm$^2$, or about 850 cm$^2$ to about 1100 cm$^2$. In some embodiments, the volume of a container containing a CAD of the present disclosure is about 1.2 L to about 1.5 L, and the surface area of the interior of the container containing a CAD is about 750 cm$^2$ to about 1400 cm$^2$, about 800 cm$^2$ to about 1300 cm$^2$, about 800 cm$^2$ to about 1200 cm$^2$, about 850 cm$^2$ to about 1200 cm$^2$, about 850 cm$^2$ to about 1150 cm$^2$, or about 850 cm$^2$ to about 1100 cm$^2$. In some embodiments, the volume of a container containing a CAD of the present disclosure is about 1.2 L to about 1.4 L, and the surface area of the interior of the container containing a CAD is about 750 cm$^2$ to about 1400 cm$^2$, about 800 cm$^2$ to about 1300 cm$^2$, about 800 cm$^2$ to about 1200 cm$^2$, about 850 cm$^2$ to about 1200 cm$^2$, about 850 cm$^2$ to about 1150 cm$^2$, or about 850 cm$^2$ to about 1100 cm$^2$. In some embodiments, the volume of a container containing a CAD of the present disclosure is about 1.1 L and the surface area of the interior of the container containing a CAD is about 750 cm$^2$ to about 820 cm$^2$ (e.g., about 750 cm$^2$, about 760 cm$^2$, about 770 cm$^2$, about 780 cm$^2$, about 790 cm$^2$, about 800 cm$^2$, about 810 cm$^2$, about 820 cm$^2$). In some embodiments, the volume of a container containing a CAD of the present disclosure is about 1.2 L and the surface area of the interior of the container containing a CAD is about 800 cm$^2$ to about 870 cm$^2$ (e.g., about 800 cm$^2$, about 810 cm$^2$, about 820 cm$^2$, about 830 cm$^2$, about 840 cm$^2$, about 850 cm$^2$, about 860 cm$^2$, about 870 cm$^2$). In some embodiments, the volume of a container containing a CAD of the present disclosure is about 1.3 L and the surface area of the interior of the container containing a CAD is about 850 cm$^2$ to about 920 cm$^2$ (e.g., about 850 cm$^2$, about 860 cm$^2$, about 870 cm$^2$, about 880 cm$^2$, about 890 cm$^2$, about 900 cm$^2$, about 910 cm$^2$, about 920 cm$^2$). In some embodiments, the volume of a container containing a CAD of the present disclosure is about 1.5 L and the surface area of the interior of the container containing a CAD is about 930 cm$^2$ to about 1000 cm$^2$ (e.g., about 930 cm$^2$, about 940 cm$^2$, about 950 cm$^2$, about 960 cm$^2$, about 970 cm$^2$, about 980 cm$^2$, about 990 cm$^2$, about 1000 cm$^2$).

In some embodiments, the surface area of the interior of a container containing a CAD of the present disclosure is greater than the surface area of the interior of the container containing a CAD (e.g., third container) of the INTERCEPT® Blood System (Cerus Corp.) Dual Storage Processing Set, Part Number INT2510. In some embodiments, the surface area of the interior of a container containing a CAD of the present disclosure is at least 3%, at least 5%, at least 10%, at least 15%, at least 20%, at least 25%, at least 30%, at least 35%, at least 40%, at least 45%, at least 50%, at least 55%, at least 60%, at least 65%, or at least 70% greater than the surface area of the interior of the container containing a CAD of the INTERCEPT® Blood System Dual Storage Processing Set, Part Number INT2510. In some embodiments, the surface area of the interior of a container containing a CAD of the present disclosure is less than 75%, less than 70%, less than 65%, less than 60%, less than 55%, less than 50%, less than 45%, less than 40%, less than 35%, less than 30%, less than 25%, less than 20%, less than 15%, or less than 10% greater than the surface area of the interior of the container containing a CAD of the INTERCEPT® Blood System Dual Storage Processing Set, Part Number INT2510. That is, the surface area of the interior of a container containing a CAD of the present disclosure can be any surface area within a range having an upper limit of 75%, 70%, 65%, 60%, 55%, 50%, 45%, 40%, 35%, 30%, 25%, 20%, 15%, or 10% greater than the surface area of the interior of the container containing a CAD of the INTERCEPT® Blood System Dual Storage Processing Set, Part Number INT2510, and an independently selected lower limit of 3%, 5%, 10%, 15%, 20%, 25%, 30%, 35%, 40%, 45%, 50%, 55%, 60%, 65%, or 70% greater than the surface area of the interior of the container containing a CAD of the INTERCEPT® Blood System Dual Storage Processing Set, Part Number INT2510, wherein the upper limit is greater than the lower limit. In some embodiments, the surface area of the interior of a container containing a CAD of the present disclosure is about 5% to about 70%, about 5% to about 65%, about 5% to about 60%, about 5% to about 55%, about 5% to about 50%, about 5% to about 45%, about 5% to about 40%, about 5% to about 35%, about 5% to about 30%, about 5% to about 25%, about 5% to about 20%, about 5% to about 15%, about 5% to about 10%, about 10% to about 70%, about 10% to about 65%, about 10% to about 60%, about 10% to about 55%, about 10% to about 50%, about 10% to about 45%, about 10% to about 40%, about 10% to about 35%, about 10% to about 30%, about 10% to about 25%, about 10% to about 20%, about 10% to about 15%, about 15% to about 70%, about 15% to about 65%, about 15% to about 60%, about 15% to about 55%, about 15% to about 50%, about 15% to about 45%, about 15% to about 40%, about 15% to about 35%, about 15% to about 30%, about 15% to about 25%, about 15% to about 20%, about 20% to about 70%, about 20% to about 65%, about 20% to about 60%, about 20% to about 55%, about 20% to about 50%, about 20% to about 45%, about 20% to about 40%, about 20% to about 35%, about 20% to about 30%, about 20% to about 25%, about 25% to about 70%, about 25% to about 65%, about 25% to about 60%, about 25% to about 55%, about 25% to about 50%, about 25% to about 45%, about 25% to about 40%, about 25% to about 35%, about 25% to about 30%, about 30% to about 70%, about 30% to about 65%, about 30% to about 60%, about 30% to about 55%, about 30% to about 50%, about 30% to about 45%, about 30% to about 40%, about 30% to about 35%, about 35% to about 70%, about 35% to about 65%, about 35% to about 60%, about 35% to about 55%, about 35% to about 50%, about 35% to about 45%, about 35% to about 40%, about 40% to about 70%, about 40% to about 65%, about 40% to about 60%, about 40% to about 55%, about 40% to about 50%, about 40% to about 45%, about 45% to about 70%, about 45% to about 65%, about 45% to about 60%, about 45% to about 55%, about 45% to about 50%, about 50% to about 70%, about 50% to about 60%, or about 50% to about 70% greater than the surface area of the interior of the container containing a CAD of the INTERCEPT® Blood System Dual Storage Processing Set, Part Number INT2510.

The indicated surface area of the interior of a container containing a CAD (e.g., third container) of the present disclosure may be an approximate surface area. For example, the inner surface of a container containing a CAD, in which the container comprises a hemocompatible bag (e.g., PVC based bag, EVA based bag, polyolefin based bag) may exhibit an amount of stretching and therefore an amount of surface area variation relative to the container in an unstretched state. In some embodiments, the surface area of the interior of a container containing a CAD of the present disclosure may comprise an indicated surface area plus or minus some amount. For example, in some embodiments, the surface area of the interior of a container containing a CAD of the present disclosure is about 750 $cm^2$, about 800 $cm^2$, about 850 $cm^2$, about 900 $cm^2$, about 950 $cm^2$, about 1000 $cm^2$, about 1050 $cm^2$, about 1100 $cm^2$, about 1150 $cm^2$, about 1200 $cm^2$, about 1300 $cm^2$, or about 1400 $cm^2$, each ±5 $cm^2$. In some embodiments, the surface area of the interior of a container containing a CAD of the present disclosure is about 750 $cm^2$, about 800 $cm^2$, about 850 $cm^2$, about 900 $cm^2$, about 950 $cm^2$, about 1000 $cm^2$, about 1050 $cm^2$, about 1100 $cm^2$, about 1150 $cm^2$, about 1200 $cm^2$, about 1300 $cm^2$, or about 1400 $cm^2$, each ±10 $cm^2$. In some embodiments, the surface area of the interior of a container containing a CAD of the present disclosure is about 750 $cm^2$, about 800 $cm^2$, about 850 $cm^2$, about 900 $cm^2$, about 950 $cm^2$, about 1000 $cm^2$, about 1050 $cm^2$, about 1100 $cm^2$, about 1150 $cm^2$, about 1200 $cm^2$, about 1300 $cm^2$, or about 1400 $cm^2$, each ±15 $cm^2$. In some embodiments, the surface area of the interior of a container containing a CAD of the present disclosure is about 750 $cm^2$, about 800 $cm^2$, about 850 $cm^2$, about 900 $cm^2$, about 950 $cm^2$, about 1000 $cm^2$, about 1050 $cm^2$, about 1100 $cm^2$, about 1150 $cm^2$, about 1200 $cm^2$, about 1300 $cm^2$, or about 1400 $cm^2$, each ±20 $cm^2$. In some embodiments, the surface area of the interior of a container containing a CAD of the present disclosure is about 750 $cm^2$, about 800 $cm^2$, about 850 $cm^2$, about 900 $cm^2$, about 950 $cm^2$, about 1000 $cm^2$, about 1050 $cm^2$, about 1100 $cm^2$, about 1150 $cm^2$, about 1200 $cm^2$, about 1300 $cm^2$, or about 1400 $cm^2$, each ±25 $cm^2$. In some embodiments, the volume of a container containing a CAD of the present disclosure is about 1.1 L and the surface area of the interior of the container containing a CAD is about 750 $cm^2$, about 760 $cm^2$, about 770 $cm^2$, about 780 $cm^2$, about 790 $cm^2$, about 800 $cm^2$, about 810 $cm^2$, or about 820 $cm^2$ (e.g., ±5 $cm^2$, ±10 $cm^2$, ±15 $cm^2$, ±20 $cm^2$, ±25 $cm^2$). In some embodiments, the volume of a container containing a CAD of the present disclosure is about 1.2 L and the surface area of the interior of the container containing a CAD is about 800 $cm^2$, about 810 $cm^2$, about 820 $cm^2$, about 830 $cm^2$, about 840 $cm^2$, about 850 $cm^2$, about 860 $cm^2$, or about 870 $cm^2$ (e.g., ±5 $cm^2$, ±10 $cm^2$, ±15 $cm^2$, ±20 $cm^2$, ±25 $cm^2$). In some embodiments, the volume of a container containing a CAD of the present disclosure is about 1.3 L and the surface area of the interior of the container containing a CAD is about 850 $cm^2$, about 860 $cm^2$, about 870 $cm^2$, about 880 $cm^2$, about 890 $cm^2$, about 900 $cm^2$, about 910 $cm^2$, or about 920 $cm^2$ (e.g., ±5 $cm^2$, ±10 $cm^2$, ±15 $cm^2$, ±20 $cm^2$, ±25 $cm^2$). In some embodiments, the volume of a container containing a CAD of the present disclosure is about 1.5 L and the surface area of the interior of the container containing a CAD is about 930 $cm^2$, about 940 $cm^2$, about 950 $cm^2$, about 960 $cm^2$, about 970 $cm^2$, about 980 $cm^2$, about 990 $cm^2$, or about 1000 $cm^2$ (e.g., ±5 $cm^2$, ±10 $cm^2$, ±15 $cm^2$, ±20 $cm^2$, ±25 $cm^2$). In some embodiments, the surface area of the interior of a container containing a CAD of the present disclosure is about 750 $cm^2$±1%, ±2%, ±3%, ±4%, or ±5%.

In some embodiments, the surface area of the interior of a container containing a CAD of the present disclosure is about 800 cm$^2$±1%, ±2%, ±3%, ±4%, or ±5%. In some embodiments, the surface area of the interior of a container containing a CAD of the present disclosure is about 850 cm$^2$±1%, ±2%, ±3%, ±4%, or ±5%. In some embodiments, the surface area of the interior of a container containing a CAD of the present disclosure is about 900 cm$^2$±1%, ±2%, ±3%, ±4%, or ±5%. In some embodiments, the surface area of the interior of a container containing a CAD of the present disclosure is about 950 cm$^2$±1%, ±2%, ±3%, ±4%, or ±5%. In some embodiments, the surface area of the interior of a container containing a CAD of the present disclosure is about 1000 cm$^2$±1%, ±2%, ±3%, ±4%, or ±5%. In some embodiments, the surface area of the interior of a container containing a CAD of the present disclosure is about 1050 cm$^2$±1%, ±2%, ±3%, ±4%, or ±5%. In some embodiments, the surface area of the interior of a container containing a CAD of the present disclosure is about 1100 cm$^2$±1%, ±2%, ±3%, ±4%, or ±5%. In some embodiments, the surface area of the interior of a container containing a CAD of the present disclosure is about 1150 cm$^2$±1%, ±2%, ±3%, ±4%, or ±5%. In some embodiments, the surface area of the interior of a container containing a CAD of the present disclosure is about 1200 cm$^2$±1%, ±2%, ±3%, ±4%, or ±5%. In some embodiments, the volume of a container containing a CAD of the present disclosure is about 1.1 L and the surface area of the interior of the container containing a CAD is about 750 cm$^2$, about 760 cm$^2$, about 770 cm$^2$, about 780 cm$^2$, about 790 cm$^2$, about 800 cm$^2$, about 810 cm$^2$, or about 820 cm$^2$ (e.g., ±1%, ±2%, ±3%, ±4%, or ±5%). In some embodiments, the volume of a container containing a CAD of the present disclosure is about 1.2 L and the surface area of the interior of the container containing a CAD is about 800 cm$^2$, about 810 cm$^2$, about 820 cm$^2$, about 830 cm$^2$, about 840 cm$^2$, about 850 cm$^2$, about 860 cm$^2$, or about 870 cm$^2$ (e.g., ±1%, ±2%, ±3%, ±4%, or ±5%). In some embodiments, the volume of a container containing a CAD of the present disclosure is about 1.3 L and the surface area of the interior of the container containing a CAD is about 850 cm$^2$, about 860 cm$^2$, about 870 cm$^2$, about 880 cm$^2$, about 890 cm$^2$, about 900 cm$^2$, about 910 cm$^2$, or about 920 cm$^2$ (e.g., ±1%, ±2%, ±3%, ±4%, or ±5%). In some embodiments, the volume of a container containing a CAD of the present disclosure is about 1.5 L and the surface area of the interior of the container containing a CAD is about 930 cm$^2$, about 940 cm$^2$, about 950 cm$^2$, about 960 cm$^2$, about 970 cm$^2$, about 980 cm$^2$, about 990 cm$^2$, or about 1000 cm$^2$ (e.g., ±1%, ±2%, ±3%, ±4%, or ±5%). In some embodiments, the surface area of the interior of a container containing a CAD of the present disclosure may refer to the inner surface area of the container.

In some embodiments, a platelet composition of the present disclosure comprises at least (e.g., greater than) about 6.0×10$^{11}$ platelets, at least about 6.5×10$^{11}$ platelets, at least about 7.0×10$^{11}$ platelets, at least about 7.5×10$^{11}$ platelets, at least about 8.0×10$^{11}$ platelets, at least about 8.5×10$^{11}$ platelets, at least about 9.0×10$^{11}$ platelets, at least about 9.5×10$^{11}$ platelets, at least about 10.0×10$^{11}$ platelets, at least about 10.5×10$^{11}$ platelets, at least about 11.0×10$^{11}$ platelets, at least about 11.5×10$^{11}$ platelets, or at least about 12.0×10$^{11}$ platelets. In some embodiments, a platelet composition of the present disclosure comprises less than about any of the following numbers of platelets: 12.0×10$^{11}$, 11.5×10$^{11}$, 11.0×10$^{11}$, 10.5×10$^{11}$, 10.0×10$^{11}$, 9.5×10$^{11}$, 9.0×10$^{11}$, 8.5×10$^{11}$, 8.0×10$^{11}$, 7.5×10$^{11}$, 7.0×10$^{11}$, or 6.5×10$^{11}$. In some embodiments, a platelet composition of the present disclosure comprises greater than about any of the following numbers of platelets: 6.0×10$^{11}$, 6.5×10$^{11}$, 7.0×10$^{11}$, 7.5×10$^{11}$, 8.0×10$^{11}$, 8.5×10$^{11}$, 9.0×10$^{11}$, 9.5×10$^{11}$, 10.0×10$^{11}$, 10.5×10$^{11}$, 11.0×10$^{11}$, or 11.5×10$^{11}$. That is, a platelet composition of the present disclosure can comprise any number of platelets within a range having an upper limit of 12.0×10$^{11}$, 11.5×10$^{11}$, 11.0×10$^{11}$, 10.5×10$^{11}$, 10.0×10$^{11}$, 9.5×10$^{11}$, 9.0×10$^{11}$, 8.5×10$^{11}$, 8.0×10$^{11}$, 7.5×10$^{11}$, 7.0×10$^{11}$, or 6.5×10$^{11}$ and an independently selected lower limit of 6.0×10$^{11}$, 6.5×10$^{11}$, 7.0×10$^{11}$, 7.5×10$^{11}$, 8.0×10$^{11}$, 8.5×10$^{11}$, 9.0×10$^{11}$, 9.5×10$^{11}$, 10.0×10$^{11}$, 10.5×10$^{11}$, 11.0×10$^{11}$, or 11.5×10$^{11}$, wherein the upper limit is greater than the lower limit. In certain embodiments, a platelet composition of the present disclosure comprises about 6.0×10$^{11}$ to about 12.0×10$^{11}$ platelets. In some embodiments, a platelet composition of the present disclosure comprises greater than about 6.0×10$^{11}$ to about 12.0×10$^{11}$ platelets. In some embodiments, a platelet composition of the present disclosure comprises about 6.5×10$^{11}$ to about 12.0×10$^{11}$ platelets. In some embodiments, a platelet composition of the present disclosure comprises about 7.0×10$^{11}$ to about 12.0×10$^{11}$ platelets. In some embodiments, a platelet composition of the present disclosure comprises about 7.5×10$^{11}$ to about 12.0×10$^{11}$ platelets. In some embodiments, a platelet composition of the present disclosure comprises about 8.0×10$^{11}$ to about 12.0×10$^{11}$ platelets. In some embodiments, a platelet composition of the present disclosure comprises about 8.5×10$^{11}$ to about 12.0×10$^{11}$ platelets. In some embodiments, a platelet composition of the present disclosure comprises about 9.0×10$^{11}$ to about 12.0×10$^{11}$ platelets. In some embodiments, a platelet composition of the present disclosure comprises about 6.0×10$^{11}$ to about 11.0×10$^{11}$ platelets. In some embodiments, a platelet composition of the present disclosure comprises about 6.0×10$^{11}$ to about 10.0×10$^{11}$ platelets. In some embodiments, a platelet composition of the present disclosure comprises about 6.0×10$^{11}$ to about 9.0×10$^{11}$ platelets. In some embodiments, a platelet composition of the present disclosure comprises about 6.0×10$^{11}$ to about 8.0×10$^{11}$ platelets.

In some embodiments, a platelet composition of the present disclosure has a volume of at least about 250 mL, at least about 300 mL, at least about 350 mL, at least about 400 mL, at least about 450 mL, at least about 500 mL, at least about 550 mL, at least about 600 mL, or at least about 650 mL. In some embodiments, a platelet composition of the present disclosure has a volume of less than about 650 mL. In some embodiments, a platelet composition of the present disclosure has a volume that is less than about any of the following volumes (in mL): 750, 700, 650, 600, 550, 500, 450, 400, 350, or 300. In some embodiments, a platelet composition of the present disclosure has a volume that is greater than about any of the following volumes (in mL): 250, 300, 350, 400, 450, 500, 550, 600, 650, or 700. That is, a platelet composition of the present disclosure can be of any volume within a range of volumes having an upper limit of 750, 700, 650, 600, 550, 500, 450, 400, 350, or 300 mL and an independently selected lower limit of 250, 300, 350, 400, 450, 500, 550, 600, 650, or 700 mL, wherein the upper limit is greater than the lower limit. In certain embodiments, a platelet composition of the present disclosure has a volume of about 350 mL to about 650 mL. In certain embodiments, a platelet composition of the present disclosure has a volume of about 300 mL to about 650 mL. In certain embodiments, a platelet composition of the present disclosure has a volume of about 250 mL to about 650 mL. In certain embodiments, a platelet composition of the present disclosure has a volume of about 250 mL to about 450 mL. In certain embodiments, a platelet composition of the present disclosure has a volume of about 250 mL to about 400 mL. In certain embodiments, a platelet composition of the present disclosure has a volume of about 300 mL to about 450 mL.

In some embodiments, a platelet composition of the present disclosure comprises platelets suspended in a suspension medium. In some embodiments, a platelet composition of the present disclosure comprises plasma. In some embodiments, a platelet composition of the present disclosure comprises platelets suspended in 100% plasma. In some embodiments, a platelet composition of the present disclosure comprises platelets suspended in a suspension medium consisting essentially of plasma. In some embodiments, a platelet composition of the present disclosure does not comprise platelet additive solution. In other embodiments, a platelet composition of the present disclosure comprises platelet additive solution (PAS). For example, in some embodiments, a platelet composition of the present disclosure comprises about 53% to about 68% platelet additive solution. A variety of platelet additive solutions suitable for use (e.g., approved by one or more regulatory authorities) are known in the art. Non-limiting examples of a platelet additive solution include the InterSol® solution (Fenwal, a Fresenius Kabi Company; Lake Zurich, Ill.), T-PAS+™ solution (Terumo BCT, Inc., Lakewood, Colo.), PAS III M™ solution (Grifols®, Barcelona, Spain), SSP+™ solution (Macopharma, Tourcoing, France), and Composol™ solution (Fresenius Kabi). In some embodiments, a platelet composition of the present disclosure comprises about 32% to about 47% plasma.

In some embodiments, the methods further include transferring the pathogen-inactivated platelet composition under sterile conditions from the container containing the CAD to one or more storage containers (e.g., as illustrated in FIGS. 1-4). For example, pathogen-inactivated platelet composition can be transferred under sterile conditions from the container containing the CAD to one storage container (see, e.g., FIG. 1 for an exemplary processing set), two storage containers (see, e.g., FIG. 2 for an exemplary processing set), or three storage containers (see, e.g., FIGS. 3 & 4 for exemplary processing sets). In some embodiments, a platelet composition of the present disclosure may be provided by collecting one or more platelet donations from one or more donors.

In some embodiments, a platelet composition of the present disclosure may be provided by pooling platelets from multiple (e.g., two or more) donations. The term "pooled platelet preparation" refers to a preparation of platelets comprising platelets obtained from more than one donation, such as an apheresis platelet donation, and subsequently combined (e.g., in a single container). Generally, the platelet donations are obtained from different donors. Platelets may be pooled at any stage after donation and prior to therapeutic use, including but not limited to pooling before or after any addition of additive solution, before or after any storage period, and before or after any pathogen inactivation treatment or process. The platelets may be combined into any container suitable for platelet preparations and of sufficient size to accommodate the platelet volume, such as for example, by sterile connecting the containers of two platelet preparations (e.g., with connecting tubing) and transferring the platelets from one container into the other, or by sterile connecting the containers of two platelet preparations to a third container (e.g., with connecting tubing) and transferring the platelets into the third container.

In some embodiments, a platelet composition of the present disclosure comprises one or more, two or more, or three or more platelet donations. In some embodiments, a pathogen-inactivated platelet composition of the present disclosure refers to one or more pathogen-inactivated platelet units suitable for infusion (e.g., one pathogen-inactivated platelet unit suitable for infusion), two pathogen-inactivated platelet units suitable for infusion, or three or more pathogen-inactivated platelet units suitable for infusion (e.g., three pathogen-inactivated platelet units suitable for infusion). In some embodiments, a pathogen-inactivated platelet unit suitable for infusion as described herein refers to a therapeutic dosage unit of pathogen-inactivated platelets. A pathogen-inactivated platelet unit suitable for infusion (e.g., therapeutic dosage unit of pathogen-inactivated platelets), generally (e.g., each) contain a specified minimum number (e.g., at least a specified minimum number) of platelets per unit to meet the therapeutic dose requirement, with such per unit or therapeutic dose criteria generally determined by governmental, regulatory or accrediting organization (e.g., industry) standards. Non-limiting examples of such standards include, for example, those set forth by FDA, EDQM, AABB, PMDA, TGA and SFDA. The specified minimum, for example, may vary by country. For example, in some embodiments, a pathogen-inactivated platelet composition (e.g., pathogen inactivated platelet unit suitable for infusion, therapeutic dosage unit) comprises at least about $2.0 \times 10^{11}$ platelets, at least about $2.2 \times 10^{11}$ platelets, at least about $2.4 \times 10^{11}$ platelets, at least about $2.5 \times 10^{11}$ platelets, at least about $2.6 \times 10^{11}$ platelets, at least about $2.7 \times 10^{11}$ platelets, at least about $2.8 \times 10^{11}$ platelets, at least about $2.9 \times 10^{11}$ platelets, or at least about $3.0 \times 10^{11}$ platelets.

In some embodiments, a platelet composition of the present disclosure can be prepared from an apheresis donation. Apheresis generally refers to automated blood collection device that uses a centrifugal or filtration separation to automatically withdraw whole blood from a donor, separate the whole blood into blood components, collect certain of the components (e.g., platelets), and return to the donor the remainder of the whole blood and remaining uncollected blood components. Plateletpheresis is the collection of platelets using such an automated blood cell separator device, which results in obtaining a high yield of platelets (e.g., apheresis platelets) from a single donor. Some automated blood cell separator devices are capable of collection procedures not only for single platelet units, but also double and triple platelet units. Apheresis collection devices are well known in the art, with several such devices commercially available, including for example, the Amicus® system (Fenwal, Inc), the Trima Accel® system (Terumo BCT) and the MCS®+9000 mobile system (Haemonetics, Inc).

In some embodiments, a platelet composition of the present disclosure can be prepared from a whole blood donation. Collection of platelets from donated whole blood donation is generally in the form of platelet concentrates (PC), obtained using processing methods such as a buffy coat or platelet rich plasma method, and such PC may be pooled to generate a platelet unit of sufficient therapeutic dosage for transfusion. In general, PC from four to six individual donors of compatible blood types are combined to produce a single platelet unit of sufficient therapeutic dosage for transfusion.

The present disclosure may, in certain embodiments, refer in various ways to platelet compositions collected from a donor (e.g., platelet donations, platelet preparations), such as for example as platelet donations or platelet preparations collected, with or without further processing (e.g., leukofiltration). Generally, reference to platelet donations or platelet preparations collected from a donor is prior to any pooling or combining step with additional platelets (e.g., from a different donor, such as a second donor or third donor) that may provide pooled platelet preparation.

In some embodiments, the methods further include, prior to mixing a platelet composition with a pathogen inactivation compound (PIC), sterilely connecting a container containing a platelet composition of the present disclosure to a container containing a PIC of the present disclosure. For example, in some embodiments, the container with the platelet composition can be connected to the container with the PIC via sterile tubing. In some embodiments, the platelet composition is mixed with the PIC prior to or during transferring the platelet composition into a container for photochemical inactivation (i.e., photochemical inactivation of a pathogen, if present in the platelet composition). In some embodiments, the platelet composition is flowed through the container containing the PIC into a separate container for photochemical inactivation. In other embodiments, the container containing the platelet composition and the container containing the PIC can each be sterilely connected to a container for photochemical inactivation. This could, for instance, permit the platelet composition and the PIC to flow into the container for photochemical inactivation, upon which mixing occurs (e.g., prior to photoillumination of the photochemical inactivation container).

In some embodiments, the methods further include, after transferring the pathogen-inactivated platelet composition under sterile conditions from the container containing the CAD to one or more storage containers, storing the pathogen-inactivated platelet composition in the one or more storage containers. Storing the pathogen-inactivated platelet composition in the one or more storage containers may be under any suitable conditions (e.g., temperature, agitation, storage period). In some embodiments, after transferring a pathogen-inactivated platelet composition of the present disclosure from the CAD container to one or more storage containers, the pathogen-inactivated platelet composition is stored in the one or more storage containers for at least 5 days at room temperature (e.g., from about 20° C. to about 25° C., such as about 22° C.), at least 6 days at room temperature, or at least 7 days at room temperature. In some embodiments, after transferring a pathogen-inactivated platelet composition of the present disclosure from the CAD container to one or more storage containers, the pathogen-inactivated platelet composition is stored in the one or more storage containers for about 5 days, about 6 days, or about 7 days at room temperature (e.g., as described above). In some embodiments, after transferring a pathogen-inactivated platelet composition of the present disclosure from the CAD container to one or more storage containers, the pathogen-inactivated platelet composition is stored in the one or more storage containers for up to 7 days at room temperature (e.g., as described above).

In some embodiments, the pH of a pathogen-inactivated platelet composition of the present disclosure after storage (e.g., as described above) is greater than or equal to 6.2, greater than or equal to 6.3, greater than or equal to 6.4, greater than or equal to 6.5, greater than or equal to 6.6, greater than or equal to 6.7, greater than or equal to 6.8, greater than or equal to 6.9, or greater than or equal to 7.0. In some embodiments, the pH of a pathogen-inactivated platelet composition of the present disclosure after storage refers to the pH at room temperature (e.g., about 22° C., $pH_{22°\ C.}$). In some embodiments, the pH of a pathogen-inactivated platelet composition of the present disclosure after storage refers to a measurement taken (e.g., from a sample) from an individual pathogen-inactivated platelet composition (e.g., each pathogen-inactivated platelet composition produced). In other embodiments, the pH of a pathogen-inactivated platelet composition of the present disclosure after storage refers to an average based on measurements taken from multiple (e.g., not all) pathogen-inactivated platelet compositions (e.g., random samples of sufficient number to provide a statistically significant sampling). For example, the pH of multiple pathogen-inactivated platelet compositions may be determined during a particular period of production (e.g., 1 month of production) and tested to yield a measurement that is held to be representative of other units that were not tested. In some embodiments, each pathogen-inactivated platelet composition has a pH as provided herein. In some embodiments, at least 90%, 91%, 92%, 93%, 94%, 95%, 96%, 97%, 98% or 99% of the pathogen-inactivated platelet compositions (e.g., for multiple pathogen-inactivated platelet compositions produced during a particular period) has a pH as provided herein.

In some embodiments, after transferring a platelet composition of the present disclosure in admixture with a PIC of the present disclosure to a container containing a CAD of the present disclosure before transferring the platelet composition out of the CAD container, the platelet composition can be stored in the CAD container for between about 1 hour and about 36 hours. In some embodiments, a platelet composition can be stored in a CAD container for between about 1 hour and about 24 hours. In some embodiments, a platelet composition can be stored in a CAD container for a period of time less than about any of the following times (in hours): 36, 30, 24, 23, 22, 21, 20, 19, 18, 17, 16, 15, 14, 13, 12, 11, 10, 9, 8, 7, 6, 5, 4, 3, or 2. In some embodiments, a platelet composition can be stored in a CAD container for a period of time greater than about any of the following times (in hours): 1, 2, 3, 4, 5, 6, 7, 8, 9, 10, 11, 12, 13, 14, 15, 16, 17, 18, 19, 20, 21, 22, 23, 24, or 30. That is, a platelet composition can be stored in a CAD container for any period of time within a range of times having an upper limit of 36, 30, 24, 23, 22, 21, 20, 19, 18, 17, 16, 15, 14, 13, 12, 11, 10, 9, 8, 7, 6, 5, 4, 3, or 2 hours and an independently selected lower limit of 1, 2, 3, 4, 5, 6, 7, 8, 9, 10, 11, 12, 13, 14, 15, 16, 17, 18, 19, 20, 21, 22, 23, 24 or 30 hours, wherein the upper limit is greater than the lower limit. In some embodiments, the platelet composition can be stored in the CAD container for at least 1 hour and up to about 24 hours. In certain embodiments, the platelet composition can be stored in the CAD container for between about 4 hours and about 24 hours. In certain embodiments, the platelet composition can be stored in the CAD container for at least 6 hours and up to about 24 hours. In certain embodiments, the platelet composition can be stored in the CAD container for at least 12 hours and up to about 24 hours. In certain embodiments, the platelet composition can be stored in the CAD container for at least 6 hours and up to about 20 hours. In certain embodiments, the platelet composition can be stored in the CAD container for at least 6 hours and up to about 16 hours. In some embodiments, after transferring a platelet composition of the present disclosure in admixture with a PIC of the present disclosure to a container containing a CAD of the present disclosure before transferring the platelet composition out of the CAD container, the platelet composition can be stored in the CAD container for about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours.

A platelet composition of the present disclosure may find use in a variety of applications known in the art. In certain aspects, provided herein are methods of infusing a platelet composition of the present disclosure into a subject in need thereof. In some embodiments, the subject is a human subject. Any of the platelet compositions of the present disclosure may find use in a method of infusion.

Platelet Processing and Processing Sets and Kits

Certain aspects of the present disclosure relate to processing sets. The processing sets of the present disclosure may find use, inter alia, in preparing a pathogen-inactivated platelet composition, e.g., as described herein. Any of the exemplary components such as bags and tubings described infra may find use in the processing sets of the present disclosure.

In some embodiments, provided herein are processing sets for preparing a pathogen-inactivated platelet composition. In some embodiments, the processing sets comprise (a) a first container that contains a pathogen inactivation compound (PIC) and is suitable for combining a platelet composition with the PIC; (b) a second container, coupled to the first container, within which the platelet composition in admixture with the PIC can be photochemically inactivated; and (c) a third container containing a compound adsorption device (CAD), wherein the third container is coupled to the second container such that the photochemically inactivated platelet composition can be transferred from the second container to the third container under sterile conditions; wherein at least one of (i) and (ii) applies: (i) the volume of the third container is greater than 1.0 L (e.g., about 1.2 L or greater); and (ii) the surface area of the interior of the third container is greater than about 750 cm$^2$ (e.g., about 800 cm$^2$ or greater). In some embodiments, a third container of the present disclosure is suitable for containing any of the platelet compositions described herein. In some embodiments, a first container of the present disclosure is suitable for sterile coupling to a container containing a platelet composition as described herein.

In some embodiments, the volume of a third container of the present disclosure is greater than 1.0 L, greater than about 1.1 L, greater than about 1.2 L, greater than about 1.3 L, greater than about 1.4 L, greater than about 1.5 L, or greater than about 1.6 L. In some embodiments, the volume of a third container of the present disclosure is less than about any of the following volumes (in L): 1.6, 1.5, 1.4, 1.3, or 1.2. In some embodiments, the volume of a third container of the present disclosure is greater than about any of the following volumes (in L): 1.1, 1.2, 1.3, 1.4, or 1.5. That is, the volume of a third container of the present disclosure can be any volume within a range having an upper limit of 1.6, 1.5, 1.4, 1.3, or 1.2 L and an independently selected lower limit of 1.1, 1.2, 1.3, 1.4, or 1.5 L, wherein the upper limit is greater than the lower limit. In certain embodiments, the volume of a third container of the present disclosure is about 1.1 L to about 1.6 L, about 1.2 L to about 1.6 L, about 1.2 L to about 1.5 L, or about 1.2 L to about 1.4 L. In some embodiments, the volume of a third container of the present disclosure is about 1.1 L, about 1.2 L, about 1.3 L, about 1.4 L, about 1.5 L, or about 1.6 L.

In some embodiments, the surface area of the interior (e.g., inner surface area) of a third container of the present disclosure is greater than about 750 cm$^2$, greater than about 800 cm$^2$, greater than about 850 cm$^2$, greater than about 900 cm$^2$, greater than about 950 cm$^2$, greater than about 1000 cm$^2$, greater than about 1050 cm$^2$, greater than about 1100 cm$^2$, greater than about 1150 cm$^2$, greater than about 1200 cm$^2$, or greater than about 1300 cm$^2$. In some embodiments, the surface area of the interior of a third container of the present disclosure is less than about 1400 cm$^2$, less than about 1300 cm$^2$, less than about 1200 cm$^2$, less than about 1150 cm$^2$, less than about 1100 cm$^2$, less than about 1050 cm$^2$, less than about 1000 cm$^2$, less than about 950 cm$^2$, less than about 900 cm$^2$, less than about 850 cm$^2$, or less than about 800 cm$^2$. That is, the surface area of the interior of a third container of the present disclosure can be an surface area within a range having an upper limit of 1400 cm$^2$, 1300 cm$^2$, 1200 cm$^2$, 1150 cm$^2$, 1100 cm$^2$, 1050 cm$^2$, 1000 cm$^2$, 950 cm$^2$, 900 cm$^2$, 850 cm$^2$, or 800 cm$^2$ and an independently selected lower limit of 750 cm$^2$, 800 cm$^2$, 850 cm$^2$, 900 cm$^2$, 950 cm$^2$, 1000 cm$^2$, 1050 cm$^2$, 1100 cm$^2$, 1150 cm$^2$, 1200 cm$^2$, or 1300 cm$^2$, wherein the upper limit is greater than the lower limit. In some embodiments, the surface area of the interior of a third container of the present disclosure is about 750 cm$^2$, about 800 cm$^2$, about 850 cm$^2$, about 900 cm$^2$, about 950 cm$^2$, about 1000 cm$^2$, about 1050 cm$^2$, about 1100 cm$^2$, about 1150 cm$^2$, or about 1200 cm$^2$. In certain embodiments, the surface area of the interior of a third container of the present disclosure is about 750 cm$^2$ to about 1400 cm$^2$, about 800 cm$^2$ to about 1300 cm$^2$, about 800 cm$^2$ to about 1200 cm$^2$, about 850 cm$^2$ to about 1200 cm$^2$, about 850 cm$^2$ to about 1150 cm$^2$, or about 850 cm$^2$ to about 1100 cm$^2$.

In some embodiments, the surface area of the interior of a third container of the present disclosure is greater than the surface area of the interior of the container containing a CAD (e.g., third container) of the INTERCEPT® Blood System (Cerus Corp.) Dual Storage Processing Set, Part Number INT2510. In some embodiments, the surface area of the interior of a third container of the present disclosure is at least 3%, at least 5%, at least 10%, at least 15%, at least 20%, at least 25%, at least 30%, at least 35%, at least 40%, at least 45%, at least 50%, at least 55%, at least 60%, at least 65%, or at least 70% greater than the surface area of the interior of the container containing a CAD of the INTERCEPT® Blood System Dual Storage Processing Set, Part Number INT2510. In some embodiments, the surface area of the interior of a third container of the present disclosure is less than 75%, less than 70%, less than 65%, less than 60%, less than 55%, less than 50%, less than 45%, less than 40%, less than 35%, less than 30%, less than 25%, less than 20%, less than 15%, or less than 10% greater than the surface area of the interior of the container containing a CAD of the INTERCEPT® Blood System Dual Storage Processing Set, Part Number INT2510. That is, the surface area of the interior of a third container of the present disclosure can be any surface area within a range having an upper limit of 75%, 70%, 65%, 60%, 55%, 50%, 45%, 40%, 35%, 30%, 25%, 20%, 15%, or 10% greater than the surface area of the interior of the container containing a CAD of the INTERCEPT® Blood System Dual Storage Processing Set, Part Number INT2510, and an independently selected lower limit of 3%, 5%, 10%, 15%, 20%, 25%, 30%, 35%, 40%, 45%, 50%, 55%, 60%, 65%, or 70% greater than the surface area of the interior of the container containing a CAD of the INTERCEPT® Blood System Dual Storage Processing Set, Part Number INT2510, wherein the upper limit is greater than the lower limit.

The indicated surface area of the interior of a third container of the present disclosure may be an approximate surface area. For example, the inner surface of a third container, in which the container comprises a hemocompatible bag (e.g., PVC based bag, EVA based bag, polyolefin based bag) may exhibit an amount of stretching and therefore an amount of surface area variation relative to the container in an unstretched state. In some embodiments, the surface area of the interior of a third container of the present disclosure may comprise an indicated surface area plus or minus some amount. For example, in some embodiments, the surface area of the interior of a third container of the present disclosure is about 750 $cm^2$, about 800 $cm^2$, about 850 $cm^2$, about 900 $cm^2$, about 950 $cm^2$, about 1000 $cm^2$, about 1050 $cm^2$, about 1100 $cm^2$, about 1150 $cm^2$, or about 1200 $cm^2$, each ±5 $cm^2$. In some embodiments, the surface area of the interior of a third container of the present disclosure is about 750 $cm^2$, about 800 $cm^2$, about 850 $cm^2$, about 900 $cm^2$, about 950 $cm^2$, about 1000 $cm^2$, about 1050 $cm^2$, about 1100 $cm^2$, about 1150 $cm^2$, or about 1200 $cm^2$, each ±10 $cm^2$. In some embodiments, the surface area of the interior of a third container of the present disclosure is about 750 $cm^2$, about 800 $cm^2$, about 850 $cm^2$, about 900 $cm^2$, about 950 $cm^2$, about 1000 $cm^2$, about 1050 $cm^2$, about 1100 $cm^2$, about 1150 $cm^2$, or about 1200 $cm^2$, each ±15 $cm^2$. In some embodiments, the surface area of the interior of a third container of the present disclosure is about 750 $cm^2$, about 800 $cm^2$, about 850 $cm^2$, about 900 $cm^2$, about 950 $cm^2$, about 1000 $cm^2$, about 1050 $cm^2$, about 1100 $cm^2$, about 1150 $cm^2$, or about 1200 $cm^2$, each ±20 $cm^2$. For example, in some embodiments, the surface area of the interior of a third container of the present disclosure is about 750 $cm^2$, about 800 $cm^2$, about 850 $cm^2$, about 900 $cm^2$, about 950 $cm^2$, about 1000 $cm^2$, about 1050 $cm^2$, about 1100 $cm^2$, about 1150 $cm^2$, or about 1200 $cm^2$, each ±25 $cm^2$. In some embodiments, the surface area of the interior of a third container of the present disclosure is about 750 $cm^2$±1%, ±2%, ±3%, ±4%, or ±5%. In some embodiments, the surface area of the interior of a third container of the present disclosure is about 800 $cm^2$±1%, ±2%, ±3%, ±4%, or ±5%. In some embodiments, the surface area of the interior of a third container of the present disclosure is about 850 $cm^2$±1%, ±2%, ±3%, ±4%, or ±5%. In some embodiments, the surface area of the interior of a third container of the present disclosure is about 900 $cm^2$±1%, ±2%, ±3%, ±4%, or ±5%. In some embodiments, the surface area of the interior of a third container of the present disclosure is about 950 $cm^2$±1%, ±2%, ±3%, ±4%, or ±5%. In some embodiments, the surface area of the interior of a third container of the present disclosure is about 1000 $cm^2$±1%, ±2%, ±3%, ±4%, or ±5%. In some embodiments, the surface area of the interior of a third container of the present disclosure is about 1050 $cm^2$±1%, ±2%, ±3%, ±4%, or ±5%. In some embodiments, the surface area of the interior of a third container of the present disclosure is about 1100 $cm^2$±1%, ±2%, ±3%, ±4%, or ±5%. In some embodiments, the surface area of the interior of a third container of the present disclosure is about 1150 $cm^2$±1%, ±2%, ±3%, ±4%, or ±5%. In some embodiments, the surface area of the interior of a third container of the present disclosure is about 1200 $cm^2$±1%, ±2%, ±3%, ±4%, or ±5%.

In some embodiments, the surface area of the interior of a third container of the present disclosure may refer to the inner surface area of the container.

In some embodiments, the third container is suitable for storing a platelet composition of the present disclosure for between about 1 hour and about 36 hours. In some embodiments, the third container is suitable for storing a platelet composition of the present disclosure for between about 1 hour and about 24 hours. In some embodiments, a third container is suitable for storing a platelet composition of the present disclosure for a period of time less than about any of the following times (in hours): 36, 30, 24, 23, 22, 21, 20, 19, 18, 17, 16, 15, 14, 13, 12, 11, 10, 9, 8, 7, 6, 5, 4, 3, or 2. In some embodiments, a third container is suitable for storing a platelet composition of the present disclosure for a period of time greater than about any of the following times (in hours): 1, 2, 3, 4, 5, 6, 7, 8, 9, 10, 11, 12, 13, 14, 15, 16, 17, 18, 19, 20, 21, 22, 23, 24, or 30. That is, a third container can be suitable for storing a platelet composition of the present disclosure for any period of time within a range of times having an upper limit of 36, 30, 24, 23, 22, 21, 20, 19, 18, 17, 16, 15, 14, 13, 12, 11, 10, 9, 8, 7, 6, 5, 4, 3, or 2 hours and an independently selected lower limit of 1, 2, 3, 4, 5, 6, 7, 8, 9, 10, 11, 12, 13, 14, 15, 16, 17, 18, 19, 20, 21, 22, 23, 24, or 30 hours, wherein the upper limit is greater than the lower limit. In certain embodiments, the third container is suitable for storing a platelet composition of the present disclosure for between about 4 hours and about 24 hours. In certain embodiments, the third container is suitable for storing a platelet composition of the present disclosure for between about 6 hours and about 24 hours. In certain embodiments, the third container is suitable for storing a platelet composition of the present disclosure for between about 12 hours and about 24 hours. In certain embodiments, the third container is suitable for storing a platelet composition of the present disclosure for between about 6 hours and about 20 hours. In certain embodiments, the third container is suitable for storing a platelet composition of the present disclosure for between about 6 hours and about 16 hours. In certain embodiments, the third container is suitable for storing a platelet composition of the present disclosure for about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours.

In some embodiments, a processing set of the present disclosure further comprises one or more fourth containers, wherein the one or more fourth containers are coupled to the third container such that the photochemically inactivated platelet composition can be transferred from the third container to the one or more fourth containers under sterile conditions to provide the pathogen-inactivated platelet composition. For example, a processing set of the present disclosure can comprise one, two, or three fourth containers. Exemplary parameters (e.g., container volume, interior surface area, number of platelets in the platelet composition, volume of the platelet composition, constituents of the platelet composition, number of platelet donations in the platelet composition, and weight (e.g., gram weight) of adsorbent beads in the CAD) for a container containing a CAD of the present disclosure (e.g., a third container) are provided supra. In some embodiments, the first container is suitable for sterile coupling (e.g., via sterile tubing) to a container containing the platelet composition. In some embodiments, one or more fourth containers of the present disclosure are suitable for storing a platelet composition, e.g., as described supra. In some embodiments, a processing set of the present disclosure further comprises any one or more of detachable clamps, frangible connectors, in-line filters, and or sampling containers (e.g., sampling pouch, diversion pouch). Non-limiting descriptions of exemplary processing sets are described infra with reference to FIGS. 1-4.

In some embodiments, a processing set of the present disclosure comprises one or more fourth containers suitable for storing a pathogen-inactivated platelet composition of the present disclosure. Storing the pathogen-inactivated platelet composition in the one or more fourth containers may be under any suitable conditions (e.g., temperature, agitation, storage period). In some embodiments, a processing set of the present disclosure comprises one or more fourth containers suitable for storing a platelet composition of the present disclosure for at least 5 days at room temperature (e.g., from about 20° C. to about 25° C., such as about 22° C.), at least 6 days at room temperature, or at least 7 days at room temperature. In some embodiments, a processing set of the present disclosure comprises one or more fourth containers suitable for storing a platelet composition of the present disclosure for up to 7 days at room temperature.

Exemplary processing set 100 is shown in FIG. 1. In some embodiments, optional bag 102 containing donor platelets is sterilely connected to set 100. Processing set 100 includes container 104 (e.g., a first container) that contains a pathogen inactivation compound (PIC, e.g., a psoralen, amotosalen) and is sterilely connected (e.g., sterile docked) to optional container (e.g., bag) 102 and connected to container (e.g., bag) 106 to allow for exposure of donor platelets to the PIC and sterile transfer of the donor platelets and PIC to container 106 for photochemical inactivation (e.g., a second container). Processing set 100 further includes CAD container 110 (e.g., CAD bag; or a third container of the present disclosure) connected to second container 106 via sterile tubing 112, which allows transfer of the donor platelets after photochemical inactivation to the CAD container. CAD container 110 contains a CAD (e.g., CAD wafer) 108, which provides for removal or reducing the concentration of pathogen inactivating compound. For example, CAD 108 can include adsorbent particles contained in a mesh pouch and/or matrix, such as for example a wafer comprising adsorbent particles and suitable binder (e.g., as described herein) that bind and/or otherwise adsorb the pathogen inactivating compound. Processing set 100 further includes fourth container 114, which is connected to CAD container 110 via sterile tubing 116.

Figure 2:
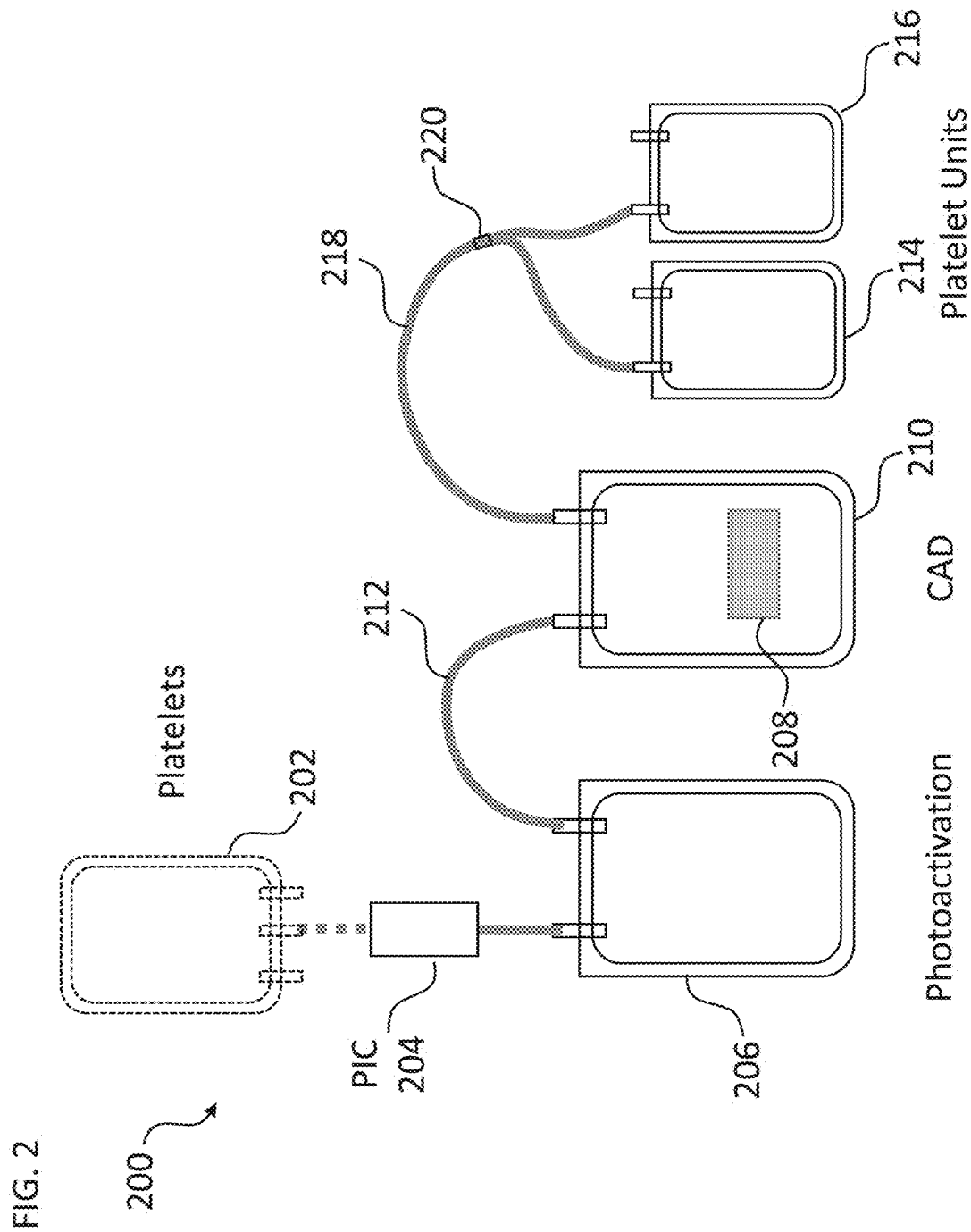
FIG. 2 shows an exemplary processing kit for use in preparing a pathogen inactivated platelet composition in accordance with some embodiments. Dotted components depict one container with platelets (e.g., donor platelets) sterilely connected to the processing kit. Abbreviations: PIC, pathogen inactivating compound; CAD, compound adsorption device. Drawing not to scale.

Exemplary processing set 200 is shown in FIG. 2. In some embodiments, optional bag 202 containing donor platelets is sterilely connected to set 200. Processing set 200 includes container 204 (e.g., a first container) that contains a pathogen inactivation compound (PIC, e.g., a psoralen, amotosalen) and is sterilely connected (e.g., sterile docked) to optional container (e.g., bag) 202 and connected to container (e.g., bag) 206 to allow for exposure of donor platelets to the PIC and sterile transfer of the donor platelets and PIC to container 206 for photochemical inactivation (e.g., a second container). Processing set 200 further includes CAD container 210 (e.g., CAD bag; or a third container of the present disclosure) connected to second container 206 via sterile tubing 212, which allows transfer of the donor platelets after photochemical inactivation to the CAD container. CAD container 210 contains a CAD (e.g., CAD wafer) 208, which provides for removal or reducing the concentration of pathogen inactivating compound. For example, CAD 208 can include adsorbent particles contained in a mesh pouch and/or matrix, such as for example a wafer comprising adsorbent particles and suitable binder (e.g., as described herein) that bind and/or otherwise adsorb the pathogen inactivating compound. Processing set 200 further includes fourth containers 214 and 216, which are connected to CAD container 210 via sterile tubing 218 and lead 220.

Figure 3:
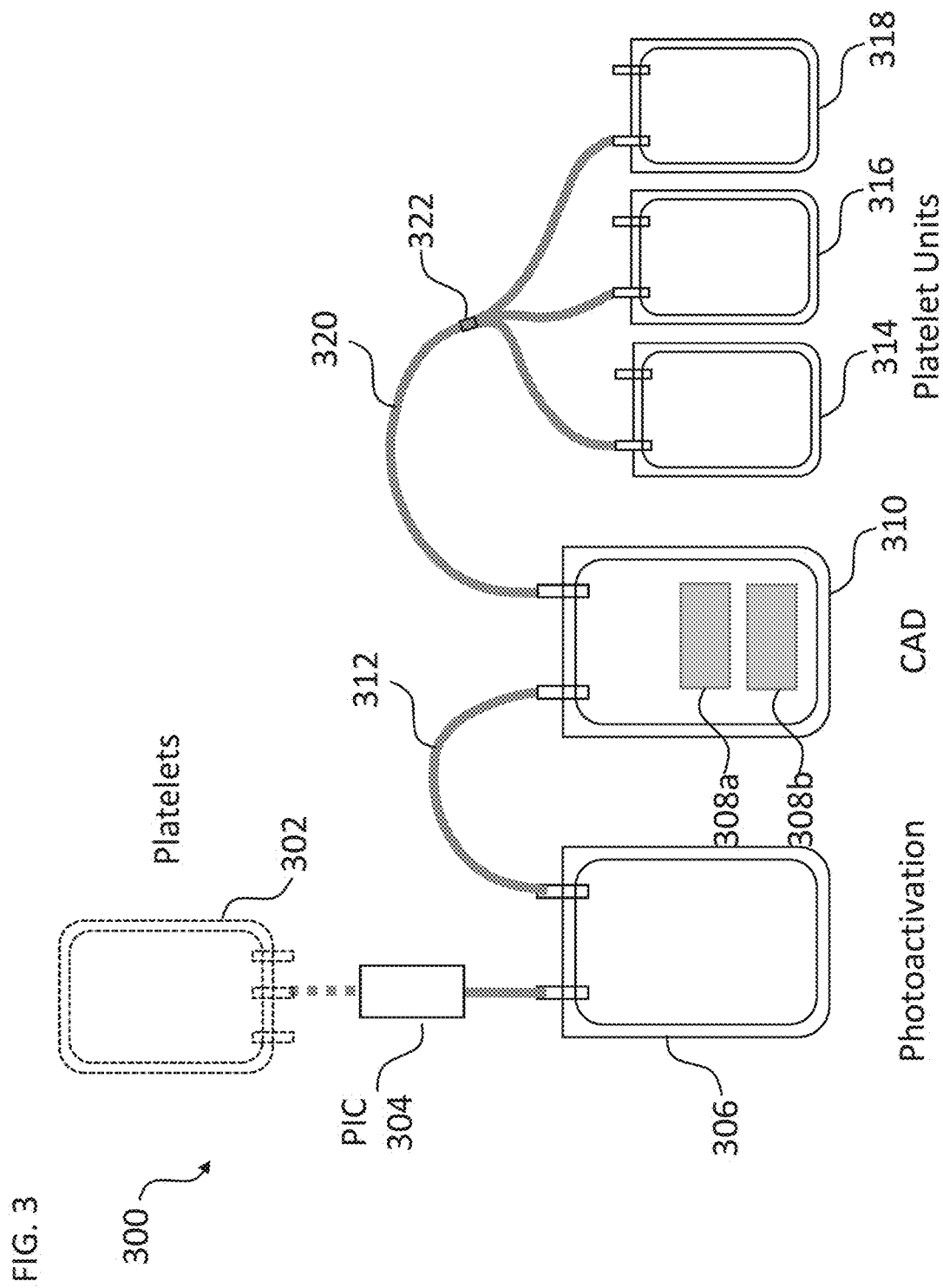
FIG. 3 shows an exemplary processing kit for use in preparing a pathogen inactivated platelet composition in accordance with some embodiments. Dotted components depict one container with platelets (e.g., donor platelets) sterilely connected to the processing kit. Abbreviations: PIC, pathogen inactivating compound; CAD, compound adsorption device. Drawing not to scale.

Exemplary processing set 300 is shown in FIG. 3. In some embodiments, optional bag 302 containing donor platelets is sterilely connected to set 300. Processing set 300 includes container 304 (e.g., a first container) that contains a pathogen inactivation compound (PIC, e.g., a psoralen, amotosalen) and is sterilely connected (e.g., sterile docked) to optional container (e.g., bag) 302 and connected to container (e.g., bag) 306 to allow for exposure of donor platelets to the PIC and sterile transfer of the donor platelets and PIC to container 306 for photochemical inactivation (e.g., a second container). Processing set 300 further includes CAD container 310 (e.g., CAD bag; or a third container of the present disclosure) connected to second container 306 via sterile tubing 312, which allows transfer of the donor platelets after photochemical inactivation to the CAD container. CAD container 310 contains two CADs (e.g., CAD wafers), 308a and 308b, which provide for removal or reducing the concentration of pathogen inactivating compound. For example, CADs 308a and 308b can each include adsorbent particles contained in a mesh pouch and/or matrix, such as for example a wafer comprising adsorbent particles and suitable binder (e.g., as described herein) that bind and/or otherwise adsorb the pathogen inactivating compound. Processing set 300 further includes fourth containers 314, 316, and 318, which are connected to CAD container 310 via sterile tubing 320 and lead 322. Advantageously, this processing set allows for preparation of larger amounts and/or volumes of platelet compositions.

Figure 4:
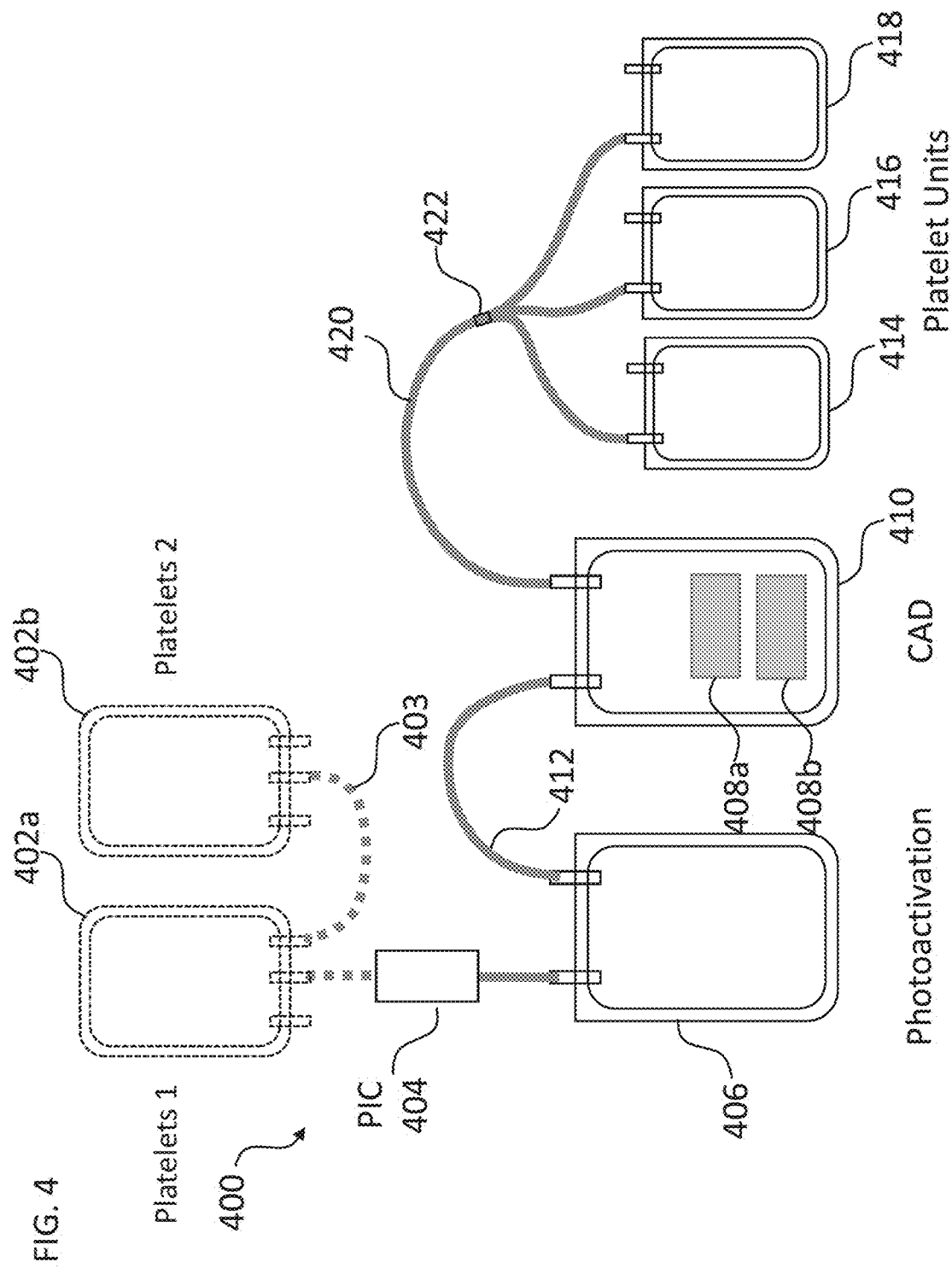
FIG. 4 shows an exemplary processing kit for use in preparing a pathogen inactivated platelet composition in accordance with some embodiments. Dotted components depict two containers with platelets (e.g., donor platelets 1, donor platelets 2) sterilely connected to each other (e.g., for pooling) and to the processing kit. Abbreviations: PIC, pathogen inactivating compound; CAD, compound adsorption device. Drawing not to scale.

Exemplary processing set 400 is shown in FIG. 4. In some embodiments, optional bags 402a and 402b, each of which contains donor platelets, are sterilely connected (e.g., sterile docked) to set 400. Instead of being sterilely connected to bag 402 containing donor platelets, container 404 is sterilely connected to two containers, 402a and 402b, containing donor platelets (e.g., first donor platelets, second donor platelets). 402a and 402b are sterilely connected to each other (e.g., for pooling) via sterile tubing 403. Advantageously, this configuration provides for a pooled platelet preparation that can be subjected to pathogen inactivation and subsequently divided into individual platelet units (e.g., 414, 416, and 418). Processing set 400 includes container 404 (e.g., a first container) that contains a pathogen inactivation compound (PIC, e.g., a psoralen, amotosalen) and is sterilely connected (e.g., sterile docked) to optional container (e.g., bag) 402 (e.g., an additional container) and connected to container (e.g., bag) 406 to allow for exposure of donor platelets to the PIC and sterile transfer of the donor platelets and PIC to container 406 for photochemical inactivation (e.g., a second container). Processing set 400 further includes CAD container 410 (e.g., CAD bag; or a third container of the present disclosure) connected to second container 406 via sterile tubing 412, which allows transfer of the donor platelets after photochemical inactivation to the CAD container. CAD container 310 contains two CADs (e.g., CAD wafers), 408a and 408b, which provide for removal or reducing the concentration of pathogen inactivating compound. For example, CADs 408a and 408b can each include adsorbent particles contained in a mesh pouch and/or matrix, such as for example a wafer comprising adsorbent particles and suitable binder (e.g., as described herein) that bind and/or otherwise adsorb the pathogen inactivating compound. Processing set 400 further includes fourth containers 414, 416, and 418, which are connected to CAD container 410 via sterile tubing 420 and lead 422.

Certain aspects of the present disclosure also relate to kits. For example, the disclosure provides a kit comprising (a) a processing set of the present disclosure (e.g., an aforementioned processing set), and (b) instructions for using the processing set to prepare a platelet composition (e.g., pathogen-inactivated platelet composition, as described herein). In some embodiments, the kit comprises a processing set for preparing a pathogen-inactivated platelet composition and instructions for using the processing set to prepare the pathogen-inactivated platelet composition, wherein, the processing set comprises: (a) a first container that contains a pathogen inactivation compound (PIC) and is suitable for combining a platelet composition with the PIC; (b) a second container, coupled to the first container, within which the platelet composition in admixture with the PIC can be photochemically inactivated; and (c) a third container containing a compound adsorption device (CAD), wherein the third container is coupled to the second container such that the photochemically inactivated platelet composition can be transferred from the second container to the third container under sterile conditions; wherein at least one of (i) and (ii) applies: (i) the volume of the third container is greater than 1.0 L (e.g., about 1.2 L or greater); and (ii) the surface area of the interior of the third container is greater than about 750 $cm^2$ (e.g., about 800 $cm^2$ or greater). In some embodiments, the processing set further comprises one or more fourth containers, wherein the one or more fourth containers are coupled to the third container such that the photochemically inactivated platelet composition can be transferred from the third container to the one or more fourth containers under sterile conditions to provide the pathogen-inactivated platelet composition. In some embodiments, the processing set comprises one fourth container. In some embodiments, the processing set comprises two fourth containers. In some embodiments, the processing set comprises three fourth containers. In some embodiments, the first container is suitable for sterile coupling to a container containing the platelet composition.

In some embodiments, the volume of the third container is greater than 1.0 L. In some embodiments, the volume of the third container is greater than 1.1 L. In some embodiments, the volume of the third container is greater than about 1.2 L. In some embodiments, the volume of the third container is about 1.3 L. In some embodiments, the volume of the third container is about 1.5 L. In some embodiments, the volume of the third container is less than about 1.6 L. In some embodiments, the volume of the third container is about 1.2 L to about 1.6 L. In some embodiments, the surface area of the interior of the third container is greater than about 750 $cm^2$. In some embodiments, the surface area of the interior of the third container is greater than about 800 $cm^2$. In some embodiments, the surface area of the interior of the third container is greater than about 850 $cm^2$. In some embodiments, the surface area of the interior of the container containing the CAD is about 900 $cm^2$. In some embodiments, the surface area of the interior of the third container is less than about 1100 $cm^2$. In some embodiments, the surface area of the interior of the container containing the CAD is about 850 $cm^2$ to about 1100 $cm^2$. In some embodiments, the CAD comprises at least about three grams of adsorbent beads. In some embodiments, the CAD comprises less than about seven grams of adsorbent beads. In some embodiments, the CAD comprises at least about seven grams of adsorbent beads. In some embodiments, the CAD comprises one wafer comprising adsorbent beads. In some embodiments, the CAD comprises more than one (e.g., two) wafer comprising adsorbent beads.

In some embodiments, the instructions indicate that the processing set is suitable for processing a platelet composition that comprises at least about $6.0 \times 10^{11}$ platelets, at least about $6.5 \times 10^{11}$ platelets, at least about $7.0 \times 10^{11}$ platelets, at least about $7.5 \times 10^{11}$ platelets, at least about $8.0 \times 10^{11}$ platelets, at least about $8.5 \times 10^{11}$ platelets, at least about $9.0 \times 10^{11}$ platelets, at least about $9.5 \times 10^{11}$ platelets, at least about $10.0 \times 10^{11}$ platelets, at least about $10.5 \times 10^{11}$ platelets, at least about $11.0 \times 10^{11}$ platelets, at least about $11.5 \times 10^{11}$ platelets, or at least about $12.0 \times 10^{11}$ platelets (e.g., about $6.0 \times 10^{11}$ to about $12.0 \times 10^{11}$ platelets). In some embodiments, the instructions indicate that the processing set is suitable for processing a platelet composition that comprises less about $12.0 \times 10^{11}$ platelets. In some embodiments, the instructions indicate that the processing set is suitable for processing a platelet composition having a volume of at least about 250 mL, at least about 300 mL, at least about 350 mL, at least about 400 mL, at least about 450 mL, at least about 500 mL, at least about 550 mL, at least about 600 mL, or at least about 650 mL (e.g., a volume of about 350 mL to about 650 mL, a volume of about 300 mL to about 650 mL, or a volume of about 250 mL to about 650 mL). In some embodiments, the instructions indicate that the processing set is suitable for processing a platelet composition having a volume of less than about 650 mL.

In some embodiments, the one or more fourth containers are suitable for storing the pathogen-inactivated platelet composition for at least 5 days at room temperature. In some embodiments, the one or more fourth containers are suitable for storing the pathogen-inactivated platelet composition for at least 6 days at room temperature. In some embodiments, the one or more fourth containers are suitable for storing the pathogen-inactivated platelet composition for at least 7 days at room temperature. In some embodiments, the one or more fourth containers are suitable for storing the pathogen-inactivated platelet composition for up to 7 days at room temperature. In some embodiments, the instructions indicate that the processing set (e.g., the one or more fourth containers) is suitable for storing the pathogen-inactivated platelet composition for at least 5 days at room temperature. In some embodiments, the instructions indicate that the processing set (e.g., the one or more fourth containers) is suitable for storing the pathogen-inactivated platelet composition for at least 6 days at room temperature. In some embodiments, the instructions indicate that the processing set (e.g., the one or more fourth containers) is suitable for storing the pathogen-inactivated platelet composition for at least 7 days at room temperature. In some embodiments, the instructions indicate that the processing set (e.g., the one or more fourth containers) is suitable for storing the pathogen-inactivated platelet composition for up to 7 days at room temperature. In some embodiments, the pH (e.g., $pH_{22°\ C.}$) of the pathogen-inactivated platelet composition after storage is ≥6.2. In some embodiments, the pH (e.g., $pH_{22°\ C.}$) of the pathogen-inactivated platelet composition after storage is ≥6.4. In some embodiments, the third container is suitable for storing the pathogen-inactivated platelet composition for between about 4 and about 24 hours.

Platelet processing as described in the present disclosure may involve the use of blood product container or blood product bag systems, which are well known in the art. In general, such systems may include more than one plastic container, typically plastic bags, where the bags are integrally connected with plastic tubing. Some of the containers described herein include such plastic bags as are known in the storage and handling of blood products (i.e., hemocompatible plastic bags), including platelet products. Blood bags typically can be designed to hold various volumes of fluid, including, but not limited to, volumes ranging from 50 mL to 2 liters, for example having up to a 350 mL capacity, 450 mL capacity, 500 mL capacity, 1 liter capacity, up to a 1.5 liter capacity, or up to a 2 liter capacity. It is understood that when a method refers to a container or bag, it includes any such plastic bags used in blood product handling. Where such bags are referred to as "pooling bag", "mixing bag", "removal bag", "product bag", "storage bag", or "illumination bag", it is understood that these bags are typical blood product handling bags, or are similar to such bags in nature. Plastic bags suitable for use according to the present disclosure include for example, those comprising PL2410, as well as other suitable plastics known in the art. Plastic bag materials include polyvinyl chloride, polyolefins, ethylene vinyl acetate, ethylene vinyl acetate blended with other plastics, and the like.

As described herein, where tubing is described as connecting e.g. two bags, such as for pooling and/or of a processing set, it is understood that the tubing may be joined at some point therebetween by another component of the connection between the two bags. For example, a removal bag connected to a product bag by a tubing includes wherein the tubing comprises a filter between the two bags, i.e. the tubing is divided by a filter such that fluid flows from one bag to the other through the tubing and filter. In one example, tubing connecting a removal bag and a product bag can include a filter to remove any loose particles from fluid flowing from the removal device to the product bag, i.e. the tubing is divided by, or interrupted by the filter between the bags. Such filters are designed to remove any small particles that may come off of the removal device, while allowing platelets to pass through the filter. The tubing between bags allows for fluid to flow from one bag to another, which can be blocked to prevent the flow until necessary, e.g. as part of the processing the fluid in one bag may be prevented from flowing to the next bag until required for the next step in a process. As such an openable seal, such as a clamp, plug, valve or the like is included in or on the tubing connecting the bags, where the clamp, plug, valve or the like can be selectively opened as required, for example to transfer the fluid from one bag to the next. In certain embodiments, the tubing between bags comprises a breakable seal, such as a breakable valve or frangible connector, whereupon breaking the breakable seal allows for the blood product solution to flow between the bags through the tubing. It is understood that the breakable seal is contained within the connection between containers, such that sterility of the system is maintained. It is also understood that a tubing comprising a filter, or a breakable seal, includes where the tubing may be interrupted by the filter or the seal, for example the tubing runs from one bag and is connected to the filter or seal (an incoming portion of the tubing), and the tubing continues from another portion of the filter or seal to another bag (an outgoing portion of the tubing). In such a configuration, fluid flows from the first bag, through the incoming portion of the tubing, through the filter or seal, and through the outgoing portion of the tubing and into the other bag.

Different containers (e.g., bags) within a blood product bag system can be used for different steps of a process. For example, a system of bags to be used for the pathogen inactivation of a preparation of platelets can include a container with pathogen inactivating compound contained within, a bag for receiving the unit of platelets (e.g., platelet donation) and a pathogen inactivating compound (e.g. an illumination bag), a bag for the illumination of the unit of platelets when the pathogen inactivation method includes illumination (e.g., an illumination bag, and typically the same bag to receive the unit of platelets and pathogen inactivating compound), a bag containing one or more compositions for the removal of pathogen inactivating compounds and/or by-products thereof (e.g., photoproducts) from the treated unit of platelets (e.g., referred to as a removal bag, compound adsorption device, CAD, CAD container), and one or more bags for containing the final platelet product, i.e. the pathogen inactivated platelet unit (e.g., therapeutic dosage unit) that has the concentration of the inactivating compound and/or by-products thereof reduced to below a desired concentration, which is ready for use or can be stored for later use (e.g., referred to as a product bag, storage bag). Each bag in the system is typically made up of a plastic material. For example, the container for containing a solution of pathogen inactivating compound can be made of a suitable plastic such as PL2411 (Baxter Healthcare), or other plastics such as polyvinyl chloride, polyolefins, ethylene vinyl acetate, ethylene vinyl acetate blended with other plastics, and the like. This container can also be overwrapped with a material that is impermeable to light of a wavelength that will activate the photoactive pathogen inactivation compound (for example suitable plastic such as PL2420, Baxter Healthcare). The illumination bag for a photoactivated pathogen inactivating compound requires a clear, durable thermoplastic material that is translucent to light of the selected wavelength. Suitable plastics that are translucent to light in the UVA wavelength range include polyvinyl chloride, polyolefins, ethylene vinyl acetate, ethylene vinyl acetate blended with other plastics, or other blends of thermoplastic polymers. Such suitable plastics include PL2410 (Baxter Healthcare) and PL732 (Baxter Healthcare). Similar materials may be used to make the removal bag and the product bag. The product bags include, for example, those made of PL2410. Suitable bag materials are discussed, for example, in PCT publication number WO 2003078023, and U.S. Pat. No. 7,025,877, the disclosures of which are hereby incorporated by reference as it relates to such bag materials and related materials. In all cases, the materials used in preparing the processing set have to be sterilizable by known methods such as steam and gamma or electron beam radiation used to ensure sterility of the processing set. While these are exemplary materials for making the bags, the methods described herein are applicable to processes using any suitable bag material as would be readily available to one skilled in the art, and can also be used with containers other than bags. The bags used for illumination, removal, and storage are also designed to allow for gases such as oxygen and carbon dioxide to go into and out of the blood bag, so that the platelets therein have adequate oxygen supply and carbon dioxide levels during the processing and storage.

Pathogen Inactivation

Blood products, including platelet-containing blood products, may contain pathogens, or may be contaminated with pathogens during processing. As such, it is desirable to subject such blood products to a pathogen inactivation process in order to reduce the risk of transfusion-transmitted diseases. Various processes and methods have been assessed to mitigate the risk of transfusion-associated disease transmission in platelet-containing blood products. Aside from screening and detection of pathogens and subsequent elimination of contaminated blood products, processes that incorporate treatments to inactivate pathogens (i.e., pathogen inactivation) that may be present are available. Ideally, such a process results in the inactivation of a broad range of pathogens such as viruses, bacteria and parasites that may be present in the blood product. In certain preferred embodiments, the methods of pathogen inactivation require addition of an amount of pathogen inactivating compound to a preparation of platelets (e.g., treating the platelet preparation). For example, pathogen inactivation may involve the addition of a low molecular weight compound that inactivates various pathogens, where a preferred method involves the addition of a photosensitizer that, when activated by illumination using light of suitable wavelengths, will inactivate a variety of pathogens that may be present. Two preferred methods that are commercially available include the addition of amotosalen or riboflavin to the platelets, with subsequent illumination with UV light. Other methods include illumination with UV light without addition of a photosensitizer, as well as illumination with other photoactive compounds, including psoralen derivatives other than amotosalen, isoalloxazines other than riboflavin, alloxazines, dyes such as phthalocyanines, phenothiazine dyes (e.g. methylene blue, azure B, azure C, thionine, toluidine blue), porphyrin derivatives (e.g. dihematoporphyrin ether, hematoporphyrin derivatives, benzoporphyrin derivatives, alkyl-substituted sapphyrin), and merocyanine 540 (Prodouz et al., Blood Cells 1992, 18(1):101-14; Sofer, Gail, BioPharm, August 2002). Other pathogen inactivation systems include, for example, those described in PCT publication numbers WO 2012071135; WO 2012018484; WO 2003090794; WO 2003049784; WO 1998018908; WO 1998030327; WO 1996008965; WO 1996039815; WO 1996039820; WO 1996040857; WO 1993000005; US patent application number US 20050202395; and U.S. Pat. Nos. 8,296,071 and 6,548,242, the disclosures of which are hereby incorporated by reference as they relate to pathogen inactivation in blood products. In some embodiments, the pathogen inactivating compound is a photoactive pathogen inactivating compound selected from the group consisting of a psoralen, an isoalloxazine, an alloxazine, a phthalocyanine, a phenothiazine, a porphyrin, and merocyanine 540. In some embodiments, the pathogen inactivating compound is a psoralen. In some embodiments, the pathogen inactivating compound is amotosalen. Where addition of a compound to the platelets is used for pathogen inactivation, whether the method requires illumination or not, in some instances it is desirable to remove any residual pathogen inactivation compound or by-product thereof.

Methods for pathogen inactivation and removal of pathogen inactivating compound as described herein are applicable to any platelet preparations, whether the platelet preparations comprise individual platelet donations (e.g., apheresis collected platelets) or pooled platelet preparations. These processes typically provide a platelet preparation that is either in about 85% to 100% plasma or has some amount of platelet additive solution added, typically in the range of 50 to 95% platelet additive solution, with the rest of the volume effectively being plasma, i.e. plasma in the range of about 5 to 50%. It is understood that a solution of pathogen inactivating compound can be added during the processing to inactivate pathogens, since pathogen inactivating compound is not typically combined in solid form, but is dissolved in a solution (for example, amotosalen is the HCl salt dissolved in a saline solution). As such, in some instances, when a platelet preparation is designated as about 100% plasma, it is understood that this means no additional platelet additive solution is included in the platelet unit. If such a preparation of platelets in about 100% plasma is treated for pathogen inactivation, some volume of the solution of pathogen inactivating compound will be included in the final product, as well as some volume of anticoagulant used in collecting the blood for isolation of platelets. While the plasma has been diluted partially with whatever amount of anticoagulant and solution that is used to contain the pathogen inactivating compound, the resulting platelet preparation including pathogen inactivation compound may be referred to as comprising about 100% plasma, or may be referred to as about 85 to 100% plasma (typically less than about 5 to 15% of the volume will comprise the solution used to deliver the pathogen inactivating compound). Platelet preparations can also be prepared with some amount of platelet additive solution, which may, for example, be added after concentrating the platelets, removing a portion of the plasma from the supernatant, and adding the desired amount of platelet additive solution to the platelet preparation. The platelet additive is added to provide the desired percentage of platelet additive solution. Such a preparation of platelets is typically adjusted so the plasma content is about 5 to 50%, with the remainder of the solution being platelet additive solution, i.e. 50 to 95% platelet additive solution. When amounts of plasma and platelet additive solutions are described, it is understood that as with platelet preparations described as being in about 100% plasma, some volume of solution containing a pathogen inactivating compound may be included in the unit of platelets containing a pathogen inactivating compound. While the solution has been diluted partially with whatever amount of solution is used to contain the pathogen inactivating compound, it is understood that, for example, a platelet preparation designated as comprising 35% plasma and 65% platelet additive solution may refer to relative amounts of plasma and platelet additive solution prior to the addition of a solution containing pathogen inactivating compound.

Some pathogen inactivation methods may require the use of a removal device, i.e. a device for reducing the concentration of pathogen inactivating compound, such as a small organic compound, e.g. platelet inactivating compound, and by-products thereof in a preparation of platelets, while substantially maintaining a desired biological activity of the platelets. In some embodiments, the removal device is referred to as a compound adsorption device (CAD), and may comprise a container (e.g., CAD container, CAD bag) containing one or more materials, such as for example, adsorbent particles (e.g., adsorbent beads), and which is suitable for also containing a preparation of platelets from which the concentration of pathogen inactivating compound and by-products thereof are to be reduced. Such a removal device is generally intended to be used in a batch mode, i.e. the device is placed in contact with the platelets, and continued contact with the removal device, e.g. with shaking to allow essentially the entirety of the solution of platelets to come into contact with the removal device over time of contact, results in reducing the levels of pathogen inactivating compound. Such batch devices entail the use of an adsorbent particle that binds the pathogen inactivation compound, and can be used by either adding adsorbent particles directly to the platelet container (e.g., bag) following illumination or transferring the platelets to a bag containing the adsorbent particles following illumination and the platelets are then agitated for a specified period of time with the platelet preparations contacting the removal device. While free adsorbent particles may be used as a removal device, such particles may be contained within a mesh pouch, such as a polyester or nylon mesh pouch, which allows for contact of the platelet solution with the adsorbent particles while containing the particles within the pouch. Alternatively, the adsorbent particles may be immobilized within a matrix, where the immobilized matrix can reside directly in the blood bag used for batch removal, or may be similarly contained within a mesh pouch. In some instances, the removal device comprises porous adsorbent particles in an amount sufficient to reduce the pathogen inactivating compound to below a desired concentration, wherein the adsorbent particles have an affinity for the pathogen inactivating compound, where it is understood such adsorbent particle can be selected to best adsorb the compound or compounds to be removed, with minimal effect on components that should not be removed or damaged by contact with the adsorbent particle. A variety of adsorbent particles are known, including generally particles made from any natural or synthetic material capable of interacting with compounds to be removed, including particulates made of natural materials such as activated carbon, silica, diatomaceous earth, and cellulose, and synthetic materials such as hydrophobic resins, hydrophilic resins or ion exchange resins. Such synthetic resins include, for example, carbonaceous materials, polystyrene, polyacrylic, polyacrylic ester, cation exchange resin, and polystyrene-divinylbenzene. Detailed description of such removal devices suitable for use in the methods as described herein can be found in PCT publication numbers WO 1996040857, WO 1998030327, WO 1999034914, and WO 2003078023, the disclosures of which are hereby incorporated by reference with respect to the discussion of such removal devices and the adsorbent particles and other materials used to prepare such devices. Exemplary adsorbent particles include, but are not limited to, Amberlite (Rohm and Haas) XAD-2, XAD-4, XAD-7, XAD-16, XAD-18, XAD-1180, XAD-1600, XAD-2000, XAD-2010; Amberchrom (Toso Haas) CG-71m, CG-71c, CG-161m, CG161c; Diaion Sepabeads (Mitsubishi Chemicals) HP20, SP206, SP207, SP850, HP2MG, HP20SS, SP20MS; Dowex (Dow Chemical) XUS-40285, XUS-40323, XUS-43493 (also referred to as Optipore V493 (dry form) or Optipore L493 (hydrated form)), Optipore V503, Optipore SD-2; Hypersol Macronet (Purolite) MN-100, MN-102, MN-150, MN-152, MN-170, MN-200, MN-202, MN-250, MN-252, MN-270, MN-300, MN-400, MN-500, MN-502, Purosorb (Purolite) PAD 350, PAD 400, PAD 428, PAD 500, PAD 550, PAD 600, PAD 700, PAD 900, and PAD 950. The material used to form the immobilized matrix comprises a low melting polymer, such as nylon, polyester, polyethylene, polyamide, polyolefin, polyvinyl alcohol, ethylene vinyl acetate, or polysulfone. In one example, the adsorbent particles immobilized in a matrix are in the form of a sintered medium. While it is understood that the methods and devices described herein encompass removal devices as are known in the art, such methods and devices may be exemplified using the removal device of an amotosalen inactivated platelet product as is commercially available. Such a removal device comprises Hypersol Macronet MN-200 adsorbent contained within a sintered matrix, where the sintered matrix comprises PL2410 plastic as a binder. In one instance, the removal device comprises Hypersol Macronet MN-200 adsorbent in a sintered matrix comprising PL2410, wherein the Hypersol Macronet MN-200 is in an amount of about 3-50 grams, about 3-40 grams, about 3-30 grams, about 3-20 grams, about 3-7 grams, about 7-15 grams, about 10-20 grams, about 5-50 grams, about 5-10 grams, about 10-15 grams, about 15-20 grams, about, 20-25 grams, about 25-30 grams, about 30-35 grams, about 35-40 grams, about 40-45 grams or about 45-50 grams dry weight equivalent.

As various resins may require different processing when used to make the removal devices useful in the methods and devices as described herein, comparison of amounts of adsorbent resins described herein, unless otherwise indicated, are comparison of the dry weight of the resin. For example, the resins are dried to <5% water prior to processing, and the equivalent of the dry weight of adsorbent is used in comparing amounts of resin in use. For example, Hypersol Macronet MN-200 is processed to stabilize the adsorbent, or what is typically referred to as wetting the adsorbent, so as to be directly usable upon contact with a platelet unit. Such a wetted sample may include, for example, about 50% glycerol or other suitable wetting agent. In some embodiments, the adsorbent resin is a polystyrene-divinylbenzene resin. In some embodiments, the polystyrene-divinylbenzene resin is Hypersol Macronet MN-200. In some embodiments, the adsorbent is contained within a sintered matrix, wherein the sintered matrix comprises PL2410 binder. In some embodiments, Hypersol Macronet MN-200 adsorbent is contained within a sintered matrix to provide a removal device.

In some embodiments, a compound adsorption device of the present disclosure comprises at least about 3 grams and less than about 50 grams, at least about 3 grams and less than about 40 grams, at least about 3 grams and less than about 30 grams, at least about 3 grams and less than about 20 grams dry weight equivalent of adsorbent beads. In some embodiments, a compound adsorption device (CAD) of the present disclosure comprises at least about 3 grams of adsorbent beads. In some embodiments, a compound adsorption device of the present disclosure comprises less than about 7 grams of adsorbent beads. In some embodiments, a compound adsorption device of the present disclosure comprises at least about 7 grams of adsorbent beads. In some embodiments, a compound adsorption device of the present disclosure comprises at least about 3 grams and less than about 7 grams. In some embodiments, a compound adsorption device of the present disclosure comprises at least about 7 grams and less than about 15 grams of adsorbent beads. In some embodiments, the CAD comprises one wafer comprising adsorbent beads. In some embodiments, the CAD comprises more than one (e.g., two) wafer comprising adsorbent beads.

Platelet Units

The present disclosure also provides pathogen-inactivated platelet compositions (e.g., platelet units) suitable for infusion (e.g., infusion into a human subject), such as for example a platelet unit selected from a plurality of platelet units prepared by any of the methods of the present disclosure. The platelet units (e.g., each platelet unit) in a plurality of platelet units comprise a therapeutic dose (e.g., therapeutic dosage unit) of platelets suitable for infusion into a human subject (e.g., a subject in need of a platelet infusion). In some embodiments, the therapeutic dose comprises a minimum number (e.g., at least a minimum number) of platelets as defined by criteria (e.g., acceptance criteria) of a governmental agency, regulatory agency, institution and/or accrediting organization (e.g., governmental agency, regulatory agency, institution and/or accrediting organization for donated blood products (e.g., donated platelets)). In some embodiments, the platelet units are prepared in the country of the governmental agency, regulatory agency, institution and/or accrediting organization defining the criteria of a therapeutic dose of platelets. In some embodiments, at least about 75%, at least about 80%, at least about 85%, at least about 90%, at least about 95%, at least about 98%, at least about 99% or more of the platelet units in the plurality of platelet units comprise the minimum number of platelets of a therapeutic dose. In some embodiments, each of the platelet units in the plurality of platelet units comprises the minimum number of platelets of a therapeutic dose. In some embodiments, the minimum number of platelets in a therapeutic dose is at least about $2.0 \times 10^{11}$ platelets, at least about 2.2×10$^{11}$ platelets, at least about 2.4×10$^{11}$ platelets, at least about 2.5×10$^{11}$ platelets, at least about 2.6×10$^{11}$ platelets, at least about 2.7×10$^{11}$ platelets, at least about 2.8×10$^{11}$ platelets, at least about 2.9×10$^{11}$ platelets or at least about 3.0×10$^{11}$ platelets. In some embodiments, the platelet units in a plurality of platelet units comprise at least about 2.0×10$^{11}$ platelets, at least about 2.2×10$^{11}$ platelets, at least about 2.4×10$^{11}$ platelets, at least about 2.5×10$^{11}$ platelets, at least about 2.6×10$^{11}$ platelets, at least about 2.7×10$^{11}$ platelets, at least about 2.8×10$^{11}$ platelets, at least about 2.9×10$^{11}$ platelets or at least about 3.0×10$^{11}$ or more platelets. In some embodiments, each of the platelet units in a plurality of platelet units comprise at least about 2.0×10$^{11}$ platelets, at least about 2.2×10$^{11}$ platelets, at least about 2.4×10$^{11}$ platelets, at least about 2.5×10$^{11}$ platelets, at least about 2.6×10$^{11}$ platelets, at least about 2.7×10$^{11}$ platelets, at least about 2.8×10$^{11}$ platelets, at least about 2.9×10$^{11}$ platelets or at least about 3.0×10$^{11}$ or more platelets. In some embodiments, at least about 75% of the platelet units in a plurality of platelet units comprise at least about 2.0×10$^{11}$ platelets, at least about 2.2×10$^{11}$ platelets, at least about 2.4×10$^{11}$ platelets, at least about 2.5×10$^{11}$ platelets, at least about 2.6×10$^{11}$ platelets, at least about 2.7×10$^{11}$ platelets, at least about 2.8×10$^{11}$ platelets, at least about 2.9×10$^{11}$ platelets or at least about 3.0×10$^{11}$ or more platelets. In some embodiments, at least about 80% of the platelet units in the plurality of platelet units comprise at least about 2.0×10$^{11}$ platelets, at least about 2.2×10$^{11}$ platelets, at least about 2.4×10$^{11}$ platelets, at least about 2.5×10$^{11}$ platelets, at least about 2.6×10$^{11}$ platelets, at least about 2.7×10$^{11}$ platelets, at least about 2.8×10$^{11}$ platelets, at least about 2.9×10$^{11}$ platelets or at least about 3.0×10$^{11}$ or more platelets. In some embodiments, at least about 85% of the platelet units in the plurality of platelet units comprise at least about 2.0×10$^{11}$ platelets, at least about 2.2×10$^{11}$ platelets, at least about 2.4×10$^{11}$ platelets, at least about 2.5×10$^{11}$ platelets, at least about 2.6×10$^{11}$ platelets, at least about 2.7×10$^{11}$ platelets, at least about 2.8×10$^{11}$ platelets, at least about 2.9×10$^{11}$ platelets or at least about 3.0×10$^{11}$ or more platelets. In some embodiments, at least about 90% of the platelet units in the plurality of platelet units comprise at least about 2.0×10$^{11}$ platelets, at least about 2.2×10$^{11}$ platelets, at least about 2.4×10$^{11}$ platelets, at least about 2.5×10$^{11}$ platelets, at least about 2.6×10$^{11}$ platelets, at least about 2.7×10$^{11}$ platelets, at least about 2.8×10$^{11}$ platelets, at least about 2.9×10$^{11}$ platelets or at least about 3.0×10$^{11}$ or more platelets. In some embodiments, at least about 95% of the platelet units in the plurality of platelet units comprise at least about 2.0×10$^{11}$ platelets, at least about 2.2×10$^{11}$ platelets, at least about 2.4×10$^{11}$ platelets, at least about 2.5×10$^{11}$ platelets, at least about 2.6×10$^{11}$ platelets, at least about 2.7×10$^{11}$ platelets, at least about 2.8×10$^{11}$ platelets, at least about 2.9×10$^{11}$ platelets or at least about 3.0×10$^{11}$ or more platelets. In some embodiments, at least about 98% of the platelet units in the plurality of platelet units comprise at least about 2.0×10$^{11}$ platelets, at least about 2.2×10$^{11}$ platelets, at least about 2.4×10$^{11}$ platelets, at least about 2.5×10$^{11}$ platelets, at least about 2.6×10$^{11}$ platelets, at least about 2.7×10$^{11}$ platelets, at least about 2.8×10$^{11}$ platelets, at least about 2.9×10$^{11}$ platelets or at least about 3.0×10$^{11}$ or more platelets. In some embodiments, at least about 99% of the platelet units in the plurality of platelet units comprise at least about 2.0×10$^{11}$ platelets, at least about 2.2×10$^{11}$ platelets, at least about 2.4×10$^{11}$ platelets, at least about 2.5×10$^{11}$ platelets, at least about 2.6×10$^{11}$ platelets, at least about 2.7×10$^{11}$ platelets, at least about 2.8×10$^{11}$ platelets, at least about 2.9×10$^{11}$ platelets or at least about 3.0×10$^{11}$ or more platelets.

In another aspect, the present disclosure provides a therapeutic dosage unit of platelets suitable for infusion into a subject, wherein the therapeutic dosage unit comprises pooled platelet compositions from two or more donors, and wherein the pooled platelet compositions have been treated with a pathogen inactivating compound. In some embodiments, the platelet compositions have been treated with the pathogen inactivating compound prior to pooling. In some embodiments, the platelet compositions have been treated with the pathogen inactivating compound after pooling. In some embodiments, the pathogen inactivating compound is a photoactive pathogen inactivating compound selected from the group consisting of a psoralen, an isoalloxazine, an alloxazine, a phthalocyanine, a phenothiazine, a porphyrin, and merocyanine 540. In some embodiments, the pathogen inactivating compound is a psoralen. In some embodiments, the pathogen inactivating compound is amotosalen. In some embodiments, the platelet compositions are from donors of the same ABO blood type. In some embodiments, the platelet compositions are from donors of the same ABO and Rh type. In some embodiments, the therapeutic dosage unit of platelets comprises at least about 2.0×10$^{11}$ platelets, at least about 2.2×10$^{11}$ platelets, at least about 2.4×10$^{11}$, at least about 2.5×10$^{11}$ platelets, at least about 2.6×10$^{11}$ platelets, at least about 2.7×10$^{11}$ platelets, at least about 2.8×10$^{11}$ platelets, at least about 2.9×10$^{11}$ platelets, at least about 3.0×10$^{11}$ or more platelets. In some embodiments, the therapeutic dosage unit of platelets comprises at least 2.4×10$^{11}$ platelets. In some embodiments, the therapeutic dosage unit of platelets comprises at least 2.6×10$^{11}$ platelets. In some embodiments, the therapeutic dosage unit of platelets comprises at least 3.0×10$^{11}$ platelets. In some embodiments, the therapeutic dosage unit of platelets comprises a minimum number (e.g., at least a minimum number) of platelets as defined by criteria (e.g., acceptance criteria) of a governmental agency, regulatory agency, institution and/or accrediting organization (e.g., governmental agency, regulatory agency, institution and/or accrediting organization for donated blood products (e.g., donated platelets)). In some embodiments, the therapeutic dosage unit of platelets is prepared in the country of the governmental agency, regulatory agency, institution and/or accrediting organization defining the criteria of a therapeutic dosage unit of platelets.

The present disclosure also provides a method of infusing platelets into a subject (e.g., human subject) in need thereof, comprising infusing into the subject an aforementioned platelet unit or an aforementioned therapeutic dosage unit of platelets.

It will also be understood by those skilled in the art that changes in the form and details of the implementations described herein may be made without departing from the scope of this disclosure. In addition, although various advantages, aspects, and objects have been described with reference to various implementations, the scope of this disclosure should not be limited by reference to such advantages, aspects, and objects. Rather, the scope of this disclosure should be determined with reference to the appended claims.

The invention is illustrated further by the following examples, which are not to be construed as limiting the invention in scope or spirit to the specific procedures described in them.

EXAMPLES

Example 1: Preparation of Pathogen-Inactivated Platelets in a Double Processing Set Platelets collected by apheresis in 100% plasma were subjected to amotosalen and UVA photochemical pathogen inactivation treatment using the INTERCEPT® Blood System dual storage set (see e.g., FIG. 2) per manufacturer's instructions (Cerus Corp.), with the exception of sampling for assays. Input platelet components were free of visible aggregates and with a volume of 327 to 420 mL and platelet dose of 3.1 to $7.9 \times 10^{11}$ platelets. Input platelet count ranged from 919 to $1957 \times 10^3/\mu L$. Platelet input components were connected to the tubing of the processing set using a sterile connect device (SCD). Amotosalen was added to the component by passing the input platelets into and through the amotosalen container and into the illumination container. Air was removed from the illumination container with the mixture of platelets and amotosalen, and the tubing connecting the amotosalen container to the illumination container was sealed and the amotosalen container and the original platelet container were detached. Platelet components with amotosalen were illuminated for 3.6 to 4.3 min with a dose of 3.90 J/cm² UVA.

Following illumination, the pathogen-inactivated platelets were transferred to the container with the CAD, comprising a 1.0 L container and CAD wafer, the illumination container then was detached and discarded, and the platelets in the CAD container were placed in an incubator at 22° C. on a flatbed platelet agitator with rotation speed of ≥60 rpm. CAD processing with agitation was 22.8±0.6 hours. Sampling for post-CAD residual amotosalen concentration was 0.73±0.34 µM. The CAD container was hung and platelets were transferred by gravity into the storage container(s), air removed from storage container(s) and the empty container with the CAD was detached and discarded. Platelet components with input platelet contents of $\leq 6.0 \times 10^{11}$ platelets were transferred to a single storage container. Platelet components with input platelet contents of $\geq 6.1 \times 10^{11}$ platelets were divided evenly (by weight) into the two storage containers. All pathogen inactivated platelet components were stored under standard conditions of continuous gentle agitation at 22° C. until the end of the seventh day post-donation (Day 7).

The pH and in-vitro characteristics of the treated apheresis platelet concentrates were evaluated through day 7 using standard procedures. The Day 7 $pH_{22° C.}$ was 7.1±0.3, with three of the 67 platelet components not maintaining $pH_{22° C.} \geq 6.4$ at day 7. Additional parameters evaluated included $pO_2$ (mm Hg)=134±19, $pCO_2$ (mm Hg)=28±7, $HCO_3^-$=5.6±2.4, supernatant glucose (mg/dL)=188±67, normalized supernatant lactate (mmol/$10^6$ platelets)=11.2±3.9, normalized total ATP (nmol/$10^8$ platelets)=4.4±1.6, morphology=283±46, ESC (%)=20.5±5.6, and HSR (%)=51±12.

Example 2: Preparation of PI Treated Platelets in a Double Processing Set with Modified CAD Container In another study, the dual storage processing set (see Example 1) was used to assess the impact of the compound adsorption device (CAD) container on in vitro quality of platelets in 100% plasma subjected to pathogen inactivation at high platelet numbers. In addition to the commercially available dual storage processing set described above, which comprises a CAD in a 1.0 L CAD container, a modified dual storage processing set comprising a CAD in a larger 1.3 L CAD container (e.g., surface area of the interior greater than 800 cm²) also was constructed for the study and used for comparison.

Apheresis platelets in 100% plasma were pooled and split to generate matched pairs of approximately $8.1 \times 10^{11}$ platelets in approximately 420 mL of 100% plasma, that were subjected to amotosalen and UVA photochemical pathogen inactivation treatment as described (see e.g., Example 1) with the 1.0 L or 1.3 L CAD processing sets. Following treatment, $pH_{22° C.}$ of the pathogen-inactivated platelets was monitored to 7 days of storage.

Eight independent replicates were processed and tested. By day 7, six of eight platelet preparations processed using the dual set with 1.0 L CAD container, had a $pH_{22° C.}$ below 6.4. Surprisingly, and in contrast, the results for platelet preparations processed using the dual set with 1.3 L CAD container showed significant improvement of pH through Day 7, where eight of eight (100%) had a $pH_{22° C.}>6.4$. PCs with high dose and large volume input showed decreased pH with the current, commercially available DS set when compared to a prototype DS set with a larger CAD container. These data suggest that the CAD step can significantly impact pH outcome on Day 7.

Another pool and split study using the dual storage processing set with a CAD in the 1.3 L CAD container and high dose input platelets was performed. Following pathogen inactivation as described, the treated platelets were stored at 22° C., with $pH_{22° C.}$ and in vitro characteristics of the treated platelets measured during storage. On Day 5, all units maintained a $pH_{22° C.}>6.4$ (7.0±0.1). Some additional parameters evaluated included $pO_2$ (mm Hg)=71.5±30.9, $pCO_2$ (mm Hg)=21.4±1.1, $HCO_3^-$=3.2±1.1, supernatant glucose (mmol/L)=8.4±1.4, supernatant lactate (mmol/L platelets)=20.4±2.2, morphology=252.0±4.7, ESC (%)=27.0±3.1, and HSR (%)=47.7±10.3.

A further study was performed comparing pathogen inactivation of platelets using the commercially available dual storage processing set comprising a CAD in a 1.0 L container, with the dual storage processing set of the present disclosure comprising a CAD in a larger 1.3 L container. For this study, ABO-matches platelets in 100% plasma were pooled and split to generate units of approximately $7.1 \times 10^{11}$ to $8.0 \times 10^{11}$ (e.g., mean $7.6 \times 10^{11}$) platelets in 375 to 420 mL (e.g., mean 390 mL, 391 mL), which were subjected to pathogen inactivation treatment using the two different processing sets, and then maintained with agitation at 22° C. Prior to treatment and again at Days 5 and 7 post-treatment, samples were removed and evaluated using standard in vitro platelet quality/function assays. Data for some parameters are provided in the following table.

| | Day 1 | Day 5 | | Day 7 | |
|---|---|---|---|---|---|
| | Input | 1.0 L | 1.3 L | 1.0 L | 1.3 L |
| $pH_{22°C}$ | 7.3 ± 0.1 | 6.2 ± 0.5 | 7.1 ± 0.1 | 6.1 ± 0.3 | 6.8 ± 0.3 |
| $pCO_2$ (mmHg) | 57.5 ± 10.3 | 12.6 ± 6.7 | 22.2 ± 2.9 | 9.2 ± 7.6 | 20.3 ± 1.7 |
| $pO_2$ (mmHg) | 36.6 ± 19.7 | 136.9 ± 50.1 | 74.3 ± 9.4 | 158.7 ± 44.4 | 91.3 ± 16.3 |
| Total ATP (mmol/$10^8$ plt) | 4.5 ± 0.5 | 3.0 ± 0.5 | 4.7 ± 0.5 | 2.7 ± 0.7 | 3.8 ± 1.5 |

-continued

|  | Day 1 | Day 5 | | Day 7 | |
| --- | --- | --- | --- | --- | --- |
|  | Input | 1.0 L | 1.3 L | 1.0 L | 1.3 L |
| Morphology score (max 400) | 265 ± 13 | 203 ± 58 | 267 ± 11 | 170 ± 55 | 228 ± 46 |
| HSR (%) | 51.9 ± 5.9 | 23.4 ± 28.0 | 56.2 ± 7.3 | 21.7 ± 30.7 | 46.2 ± 24.2 |
| CD62P | 22.4 ± 5.8 | 71.0 ± 32.4 | 28.0 ± 6.3 | 77.0 ± 23.1 | 57.0 ± 22.7 |

The data indicate a beneficial outcome at Days 5 and 7 storage after using processing sets with the larger CAD container compared to the commercially available 1.0 L CAD container. For the platelets treated with processing sets comprising the larger 1.3 L CAD container, the results showed higher pH, higher pCO2, lower pO2, higher ATP, higher morphology scores, better recovery from hypotonic shock (HSR) and lower CD62P.

Example 3: Preparation of PI Treated Platelets in a Triple Processing Set

A 1.3 L capacity CAD container also was incorporated in an INTERCEPT® triple processing set (see e.g., FIGS. 3 & 4). The 1.3 L container contains two CAD wafers sealed in a mesh pouch. A study was performed to evaluate the in vitro functions of pooled apheresis platelet donations suspended in 35% plasma and 65% PAS, after treatment using the INTERCEPT® platelet processing set with triple storage containers. Pools of two apheresis platelets were used as high dose, high volume input of approximately 10.2 to $11.8 \times 10^{11}$ platelets in approximately 623 to 648 mL of 35% plasma/65% PAS-3, CAD incubation times were between 14.2 and 15.0 hours, and post-CAD amotosalen levels were ≤0.14 µM. Following pathogen inactivation, $pH_{22° C.}$ and in vitro characteristics of the treated platelets were monitored to 7 days of storage. On Day 7, all units maintained a $pH_{22° C.} > 6.4$ (7.0±0.1). Some additional parameters evaluated included pO2 (mm Hg)=135±8, pCO2 (mm Hg)=11±1, $HCO_3^- = 2 \pm 1$, supernatant glucose (mmol/L)=0.0±0.0, normalized supernatant lactate (mmol/$10^6$ platelets)=9.1±1.0, total ATP (nmol/$10^8$ platelets)=2.1±0.5, morphology=246±10, ESC (%)=14.6±3.0, and HSR (%)=32.4±3.9.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Wherever an open-ended term is used to describe a feature or element, it is specifically contemplated that a closed-ended term can be used in place of the open-ended term without departing from the spirit and scope of the disclosure. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the description and does not pose a limitation on the scope of the description unless otherwise claimed. No language in the specification should be construed as indicating any non-claimed element as essential to the practice of the methods, systems and compositions disclosed herein.

Preferred embodiments are described herein. Variations of those preferred embodiments may become apparent to those working in the art upon reading the foregoing description. It is expected that skilled artisans will be able to employ such variations as appropriate, and the practice of the methods, systems and compositions described herein otherwise than as specifically described herein. Accordingly, the methods, systems and compositions described herein include all modifications and equivalents of the subject matter recited in the claims appended hereto as permitted by applicable law. Moreover, any combination of the above-described elements in all possible variations thereof is encompassed by the description unless otherwise indicated herein or otherwise clearly contradicted by context.

LIST OF EMBODIMENTS

Embodiment 1

A method of preparing a pathogen-inactivated platelet composition, comprising:
(a) mixing a platelet composition with a pathogen inactivation compound (PIC);
(b) photochemically inactivating the platelet composition in admixture with the PIC; and
(c) transferring the resultant mixture of step (b) under sterile conditions to a container containing a compound adsorption device (CAD) to produce a pathogen-inactivated platelet composition;
wherein at least one of (i) and (ii) applies:
(i) the volume of the container containing the CAD is greater than 1.0 L; and
(ii) the surface area of the interior of the container containing the CAD is greater than about 750 $cm^2$.

Embodiment 2

The method of embodiment 1, further comprising:
(d) transferring the pathogen-inactivated platelet composition under sterile conditions from the container containing the CAD to one or more storage containers.

Embodiment 3

The method of embodiment 2, wherein the one or more storage containers is one storage container.

Embodiment 4

The method of embodiment 2, wherein the one or more storage containers is two storage containers.

Embodiment 5

The method of embodiment 2, wherein the one or more storage containers is three storage containers.

Embodiment 6

The method of any one of embodiments 1-5, wherein the volume of the container containing the CAD is greater than 1.0 L.

Embodiment 7

The method of any one of embodiments 1-6, wherein the volume of the container containing the CAD is greater than about 1.2 L.

Embodiment 8

The method of any one of embodiments 1-7, wherein the volume of the container containing the CAD is about 1.3 L.

Embodiment 9

The method of any one of embodiments 1-7, wherein the volume of the container containing the CAD is about 1.5 L.

Embodiment 10

The method of any one of embodiments 1-7, wherein the volume of the container containing the CAD is about 1.2 L to about 1.6 L.

Embodiment 11

The method of any one of embodiments 1-10, wherein the surface area of the interior of the container containing the CAD is greater than about 750 $cm^2$.

Embodiment 12

The method of any one of embodiments 1-11, wherein the surface area of the interior of the container containing the CAD is greater than about 850 $cm^2$.

Embodiment 13

The method of any one of embodiments 1-12, wherein the surface area of the interior of the container containing the CAD is about 900 $cm^2$.

Embodiment 14

The method of any one of embodiments 1-12, wherein the surface area of the interior of the container containing the CAD is about 850 $cm^2$ to about 1100 $cm^2$.

Embodiment 15

The method of any one of embodiments 1-14, wherein the platelet composition comprises at least about $6.0 \times 10^{11}$ platelets.

Embodiment 16

The method of any one of embodiments 1-14, wherein the platelet composition comprises at least about $7.0 \times 10^{11}$ platelets.

Embodiment 17

The method of any one of embodiments 1-14, wherein the platelet composition comprises at least about $8.0 \times 10^{11}$ platelets.

Embodiment 18

The method of any one of embodiments 1-14, wherein the platelet composition comprises at least about $11.0 \times 10^{11}$ platelets.

Embodiment 19

The method of any one of embodiments 1-14, wherein the platelet composition comprises about $6.0 \times 10^{11}$ to about $12.0 \times 10^{11}$ platelets.

Embodiment 20

The method of any one of embodiments 1-19, wherein the platelet composition has a volume of at least about 350 mL.

Embodiment 21

The method of any one of embodiments 1-19, wherein the platelet composition has a volume of at least about 400 mL.

Embodiment 22

The method of any one of embodiments 1-19, wherein the platelet composition has a volume of at least about 450 mL.

Embodiment 23

The method of any one of embodiments 1-19, wherein the platelet composition has a volume of at least about 500 mL.

Embodiment 24

The method of any one of embodiments 1-19, wherein the platelet composition has a volume of at least about 600 mL.

Embodiment 25

The method of any one of embodiments 1-19, wherein the platelet composition has a volume of about 350 mL to about 650 mL.

Embodiment 26

The method of any one of embodiments 1-25, wherein the platelet composition comprises plasma.

Embodiment 27

The method of embodiment 26, wherein the platelet composition does not comprise platelet additive solution.

Embodiment 28

The method of any one of embodiments 1-26, wherein the platelet composition comprises platelet additive solution.

Embodiment 29

The method of embodiment 28, wherein the platelet composition comprises about 53% to about 68% platelet additive solution.

Embodiment 30

The method of any one of embodiments 1-27, wherein the platelet composition comprises platelets suspended in a suspension medium consisting essentially of plasma.

Embodiment 31

The method of any one of embodiments 1-30, wherein the method comprises, prior to step (a), collecting one or more platelet donations from one or more donors.

Embodiment 32

The method of any one of embodiments 1-31, wherein the platelet composition is prepared from an apheresis donation.

Embodiment 33

The method of any one of embodiments 1-31, wherein the platelet composition is prepared from a whole blood donation.

Embodiment 34

The method of any one of embodiments 1-33, wherein the platelet composition comprises one platelet donation.

Embodiment 35

The method of any one of embodiments 1-33, wherein the platelet composition comprises two platelet donations.

Embodiment 36

The method of any one of embodiments 1-33, wherein the platelet composition comprises three or more platelet donations.

Embodiment 37

The method of any one of embodiments 1-36, wherein the CAD comprises at least about three grams of adsorbent beads.

Embodiment 38

The method of embodiment 37, wherein the CAD comprises less than about seven grams of adsorbent beads.

Embodiment 39

The method of any one of embodiments 1-36, wherein the CAD comprises at least about seven grams of adsorbent beads.

Embodiment 40

The method of any one of embodiments 1-39, wherein the method comprises, prior to step (a), sterilely connecting a container containing the platelet composition to a container containing the PIC.

Embodiment 41

The method of any one of embodiments 2-38, further comprising, after step (d), storing the pathogen-inactivated platelet composition in the one or more storage containers for at least 5 days at room temperature.

Embodiment 42

The method of embodiment 41, wherein the storage is for at least 6 days at room temperature.

Embodiment 43

The method of embodiment 41, wherein the storage is for at least 7 days at room temperature.

Embodiment 44

The method of any one of embodiments 41-43, wherein the storage is for up to 7 days at room temperature.

Embodiment 45

The method of any one of embodiments 41-44, wherein the pH of the pathogen-inactivated platelet composition after storage is ≥6.2.

Embodiment 46

The method of any one of embodiments 41-44, wherein the pH of the pathogen-inactivated platelet composition after storage is ≥6.4.

Embodiment 47

The method of any one of embodiments 2-46, wherein, after step (c) and before step (d), the pathogen-inactivated platelet composition is stored in the container containing the CAD for between about 4 and about 24 hours.

Embodiment 48

The method of any one of embodiments 1-47, wherein the pathogen-inactivated platelet composition is one or more pathogen-inactivated platelet units suitable for infusion.

Embodiment 49

The method of any one of embodiments 1-47, wherein the pathogen-inactivated platelet composition is one pathogen-inactivated platelet unit suitable for infusion.

Embodiment 50

The method of any one of embodiments 1-47, wherein the pathogen-inactivated platelet composition is two pathogen-inactivated platelet units suitable for infusion.

Embodiment 51

The method of any one of embodiments 1-47, wherein the pathogen-inactivated platelet composition is three pathogen-inactivated platelet units suitable for infusion.

Embodiment 52

The method of any one of embodiments 48-51, wherein the pathogen-inactivated platelet unit suitable for infusion is a therapeutic dosage unit of pathogen-inactivated platelets.

Embodiment 53

The method of any one of embodiments 1-52, wherein the pathogen-inactivated platelet composition comprises at least $2.0 \times 10^{11}$ platelets.

Embodiment 54

The method of any one of embodiments 1-52, wherein the pathogen-inactivated platelet composition comprises at least $2.4 \times 10^{11}$ platelets.

Embodiment 55

The method of any one of embodiments 1-52, wherein the pathogen-inactivated platelet composition comprises at least $3.0 \times 10^{11}$ platelets.

Embodiment 56

A pathogen-inactivated platelet composition prepared by the method of any one of embodiments 1-55.

Embodiment 57

The pathogen-inactivated platelet composition of embodiment 56, wherein the pathogen-inactivated platelet composition is one or more pathogen-inactivated platelet units suitable for infusion.

Embodiment 58

The pathogen-inactivated platelet composition of embodiment 56, wherein the pathogen-inactivated platelet composition is one pathogen-inactivated platelet unit suitable for infusion.

Embodiment 59

The pathogen-inactivated platelet composition of embodiment 56, wherein the pathogen-inactivated platelet composition is two pathogen-inactivated platelet units suitable for infusion.

Embodiment 60

The pathogen-inactivated platelet composition of embodiment 56, wherein the pathogen-inactivated platelet composition is three pathogen-inactivated platelet units suitable for infusion.

Embodiment 61

The pathogen-inactivated platelet composition of any one of embodiments 57-60, wherein the pathogen-inactivated platelet unit suitable for infusion is a therapeutic dosage unit of pathogen-inactivated platelets.

Embodiment 62

The pathogen-inactivated platelet composition of any one of embodiments 56-61, wherein the pathogen-inactivated platelet composition comprises at least $2.0 \times 10^{11}$ platelets.

Embodiment 63

The pathogen-inactivated platelet composition of any one of embodiments 56-61, wherein the pathogen-inactivated platelet composition comprises at least $2.4 \times 10^{11}$ platelets.

Embodiment 64

The pathogen-inactivated platelet composition of any one of embodiments 56-61, wherein the pathogen-inactivated platelet composition comprises at least $3.0 \times 10^{11}$ platelets.

Embodiment 65

A method of infusing a platelet composition into a subject in need thereof, the method comprising infusing into the subject a pathogen-inactivated platelet composition prepared by the method of any one of embodiments 1-55 or a pathogen-inactivated platelet unit of any one of embodiments 57-64.

Embodiment 66

A processing set for preparing a pathogen-inactivated platelet composition, comprising:
(a) a first container that contains a pathogen inactivation compound (PIC) and is suitable for combining a platelet composition with the PIC;
(b) a second container, coupled to the first container, within which the platelet composition in admixture with the PIC can be photochemically inactivated; and
(c) a third container containing a compound adsorption device (CAD), wherein the third container is coupled to the second container such that the photochemically inactivated platelet composition can be transferred from the second container to the third container under sterile conditions;
  wherein at least one of (i) and (ii) applies:
  (i) the volume of the third container is greater than 1.0 L; and
  (ii) the surface area of the interior of the third container is greater than about 750 cm$^2$.

Embodiment 67

The processing set of embodiment 66, further comprising one or more fourth containers, wherein the one or more fourth containers are coupled to the third container such that the photochemically inactivated platelet composition can be transferred from the third container to the one or more fourth containers under sterile conditions to provide the pathogen-inactivated platelet composition.

Embodiment 68

The processing set of embodiment 67, comprising one fourth container.

Embodiment 69

The processing set of embodiment 67, comprising two fourth containers.

Embodiment 70

The processing set of embodiment 67, comprising three fourth containers.

Embodiment 71

The processing set of any one of embodiments 66-70, wherein the volume of the third container is greater than 1.0 L.

Embodiment 72

The processing set of any one of embodiments 66-71, wherein the volume of the third container is greater than about 1.2 L.

Embodiment 73

The processing set of any one of embodiments 66-71, wherein the volume of the third container is about 1.3 L.

Embodiment 74

The processing set of any one of embodiments 66-71, wherein the volume of the third container is about 1.5 L.

Embodiment 75

The processing set of any one of embodiments 66-71, wherein the volume of the third container is about 1.2 L to about 1.6 L.

Embodiment 76

The processing set of any one of embodiments 66-75, wherein the surface area of the interior of the third container is greater than about 750 cm$^2$.

Embodiment 77

The processing set of any one of embodiments 66-75, wherein the surface area of the interior of the third container is greater than about 850 cm$^2$.

Embodiment 78

The processing set of any one of embodiments 66-77, wherein the surface area of the interior of the container containing the CAD is about 900 cm$^2$.

Embodiment 79

The processing set of any one of embodiments 66-77, wherein the surface area of the interior of the container containing the CAD is about 850 cm$^2$ to about 1100 cm$^2$.

Embodiment 80

The processing set of any one of embodiments 66-79, wherein the platelet composition comprises at least about $6.0 \times 10^{11}$ platelets.

Embodiment 81

The processing set of any one of embodiments 66-79, wherein the platelet composition comprises at least about $7.0 \times 10^{11}$ platelets.

Embodiment 82

The processing set of any one of embodiments 66-79, wherein the platelet composition comprises at least about $8.0 \times 10^{11}$ platelets.

Embodiment 83

The processing set of any one of embodiments 66-79, wherein the platelet composition comprises at least about $11.0 \times 10^{11}$ platelets.

Embodiment 84

The processing set of any one of embodiments 66-79, wherein the platelet composition comprises about $6.0 \times 10^{11}$ to about $12.0 \times 10^{11}$ platelets.

Embodiment 85

The processing set of any one of embodiments 66-84, wherein the platelet composition has a volume of at least about 350 mL.

Embodiment 86

The processing set of any one of embodiments 66-84, wherein the platelet composition has a volume of at least about 400 mL.

Embodiment 87

The processing set of any one of embodiments 66-84, wherein the platelet composition has a volume of at least about 450 mL.

Embodiment 88

The processing set of any one of embodiments 66-84, wherein the platelet composition has a volume of at least about 500 mL.

Embodiment 89

The processing set of any one of embodiments 66-84, wherein the platelet composition has a volume of at least about 600 mL.

Embodiment 90

The processing set of any one of embodiments 66-84, wherein the platelet composition has a volume of about 350 mL to about 650 mL.

Embodiment 91

The processing set of any one of embodiments 66-90, wherein the platelet composition comprises plasma.

Embodiment 92

The processing set of embodiment 91, wherein the platelet composition does not comprise platelet additive solution.

Embodiment 93

The processing set of any one of embodiments 66-91, wherein the platelet composition comprises platelet additive solution.

Embodiment 94

The processing set of embodiment 93, wherein the platelet composition comprises about 53% to about 68% platelet additive solution.

Embodiment 95

The processing set of any one of embodiments 66-92, wherein the platelet composition comprises platelets suspended in a suspension medium consisting essentially of plasma.

Embodiment 96

The processing set of any one of embodiments 66-95, wherein the platelet composition comprises one or more platelet donations from one or more donors.

Embodiment 97

The processing set of any one of embodiments 66-96, wherein the platelet composition is prepared from an apheresis donation.

Embodiment 98

The processing set of any one of embodiments 66-96, wherein the platelet composition is prepared from a whole blood donation.

Embodiment 99

The processing set of any one of embodiments 66-98, wherein the platelet composition comprises one platelet donation.

Embodiment 100

The processing set of any one of embodiments 66-98, wherein the platelet composition comprises two platelet donations.

Embodiment 101

The processing set of any one of embodiments 66-98, wherein the platelet composition comprises three or more platelet donations.

Embodiment 102

The processing set of any one of embodiments 66-101, wherein the CAD comprises at least about three grams of adsorbent beads.

Embodiment 103

The processing set of embodiment 102, wherein the CAD comprises less than about seven grams of adsorbent beads.

Embodiment 104

The processing set of any one of embodiments 66-102, wherein the CAD comprises at least about seven grams of adsorbent beads.

Embodiment 105

The processing set of any one of embodiments 66-104, wherein the first container is suitable for sterile coupling to a container containing the platelet composition.

Embodiment 106

The processing set of any one of embodiments 67-105, wherein the one or more fourth containers are suitable for storing the pathogen-inactivated platelet composition for at least 5 days at room temperature.

Embodiment 107

The processing set of embodiment 106, wherein the one or more fourth containers are suitable for storing the pathogen-inactivated platelet composition for at least 6 days at room temperature.

Embodiment 108

The processing set of embodiment 106, wherein the one or more fourth containers are suitable for storing the pathogen-inactivated platelet composition for at least 7 days at room temperature.

Embodiment 109

The processing set of any one of embodiments 106-108, wherein the one or more fourth containers are suitable for storing the pathogen-inactivated platelet composition for up to 7 days at room temperature.

Embodiment 110

The processing set of any one of embodiments 106-109, wherein the pH of the pathogen-inactivated platelet composition after storage is ≥6.2.

Embodiment 111

The processing set of any one of embodiments 106-109, wherein the pH of the pathogen-inactivated platelet composition after storage is ≥6.4.

Embodiment 112

The processing set of any one of embodiments 66-111, wherein the third container is suitable for storing the pathogen-inactivated platelet composition for between about 4 and about 24 hours.

Embodiment 113

The processing set of any one of embodiments 66-112, wherein the pathogen-inactivated platelet composition is one or more pathogen-inactivated platelet units suitable for infusion.

Embodiment 114

The processing set of any one of embodiments 66-112, wherein the pathogen-inactivated platelet composition is one pathogen-inactivated platelet unit suitable for infusion.

Embodiment 115

The processing set of any one of embodiments 66-112, wherein the pathogen-inactivated platelet composition is two pathogen-inactivated platelet units suitable for infusion.

Embodiment 116

The processing set of any one of embodiments 66-112, wherein the pathogen-inactivated platelet composition is three pathogen-inactivated platelet units suitable for infusion.

Embodiment 117

The processing set of any one of embodiments 113-116, wherein the pathogen-inactivated platelet unit suitable for infusion is a therapeutic dosage unit of pathogen-inactivated platelets.

Embodiment 118

The processing set of any one of embodiments 66-117, wherein the pathogen-inactivated platelet composition comprises at least $2.0 \times 10^{11}$ platelets.

Embodiment 119

The processing set of any one of embodiments 66-117, wherein the pathogen-inactivated platelet composition comprises at least $2.4 \times 10^{11}$ platelets.

Embodiment 120

The processing set of any one of embodiments 66-117, wherein the pathogen-inactivated platelet composition comprises at least $3.0 \times 10^{11}$ platelets.

What is claimed is:

1. A method of preparing a pathogen-inactivated platelet composition, comprising:
   (a) mixing a platelet composition with a pathogen inactivation compound (PIC), wherein the PIC is a psoralen, and wherein the platelet composition has a volume of about 250 mL to about 750 mL;
   (b) photochemically inactivating the platelet composition in admixture with the PIC; and
   (c) transferring the resultant mixture of step (b) under sterile conditions to a container containing a compound adsorption device (CAD) to produce a pathogen-inactivated platelet composition;
   wherein at least one of (i) and (ii) applies:
      (i) the volume of the container containing the CAD is about 1.2 L to about 1.6 L; and
      (ii) the surface area of the interior of the container containing the CAD is about 800 cm$^2$ to about 1200 cm$^2$.

2. The method of claim 1, further comprising:
   (d) transferring the pathogen-inactivated platelet composition under sterile conditions from the container containing the CAD to one or more storage containers.

3. The method of claim 2, wherein the one or more storage containers is two storage containers.

4. The method of claim 2, wherein the one or more storage containers is three storage containers.

5. The method of claim 1, wherein the volume of the container containing the CAD is about 1.2 L to about 1.6 L.

6. The method of claim 1, wherein the surface area of the interior of the container containing the CAD is about 800 cm$^2$ to about 1200 cm$^2$.

7. The method of claim 1, wherein the platelet composition comprises at least about $6.0 \times 10^{11}$ platelets.

8. The method of claim 1, wherein the method comprises, prior to step (a), collecting one or more platelet donations from one or more donors.

9. The method of claim 1, wherein the CAD comprises at least about three grams of adsorbent beads.

10. The method of claim 9, wherein the CAD comprises less than about seven grams of adsorbent beads.

11. The method of claim 1, wherein the CAD comprises at least about seven grams of adsorbent beads.

12. The method of claim 2, further comprising, after step (d), storing the pathogen-inactivated platelet composition in the one or more storage containers for at least 5 days at room temperature.

13. The method of claim 12, wherein the storage is for up to 7 days at room temperature.

14. The method of claim 12, wherein the pH of the pathogen-inactivated platelet composition after storage is ≥6.2.

15. The method of claim 1, wherein the pathogen-inactivated platelet composition is one or more pathogen-inactivated platelet units suitable for infusion.

16. The method of claim 1, wherein the platelet composition comprises about $6.0 \times 10^{11}$ to about $12.0 \times 10^{11}$ platelets.

17. The method of claim 1, wherein the platelet composition comprises plasma.

18. The method of claim 1, wherein the platelet composition comprises platelet additive solution.

19. The method of claim 12, wherein the pH of the pathogen-inactivated platelet composition after storage is ≥6.4.

20. The method of claim 15, wherein the pathogen-inactivated platelet unit suitable for infusion is a therapeutic dosage unit of pathogen-inactivated platelets.

21. The method of claim 15, wherein the pathogen-inactivated platelet unit suitable for infusion comprises at least $2.0 \times 10^{11}$ platelets.

22. The method of claim 1, wherein the platelet composition comprises at least $3.0 \times 10^{11}$ platelets.

23. The method of claim 3, wherein the platelet composition comprises less than about $8.0 \times 10^{11}$ platelets.

24. The method of claim 4, wherein the platelet composition comprises less than about $12.0 \times 10^{11}$ platelets.

25. The method of claim 1, wherein the platelet composition has a volume of about 250 mL to about 650 mL.

26. A method of preparing a pathogen-inactivated platelet composition, comprising:
   (a) mixing a platelet composition with a pathogen inactivation compound (PIC), wherein the PIC is a psoralen, and wherein the platelet composition has a volume of about 250 mL to about 750 mL;
(b) photochemically inactivating the platelet composition in admixture with the PIC;
(c) transferring the resultant mixture of step (b) under sterile conditions to a container containing a compound adsorption device (CAD) to produce a pathogen-inactivated platelet composition;
wherein the CAD comprises less than about seven grams of adsorbent beads, and at least one of (i) and (ii) applies:
   (i) the volume of the container containing the CAD is about 1.2 to about 1.6 L; and
   (ii) the surface area of the interior of the container containing the CAD is about 800 $cm^2$ to about 1200 $cm^2$; and
(d) transferring the pathogen-inactivated platelet composition under sterile conditions from the container containing the CAD to two storage containers,
wherein the pathogen-inactivated platelet composition in each of said two storage containers is a therapeutic dosage unit of pathogen-inactivated platelets suitable for infusion.

27. The method of claim 26, wherein the platelet composition has a volume of about 250 mL to about 650 mL.

28. A method of preparing a pathogen-inactivated platelet composition, comprising:

(a) mixing a platelet composition with a pathogen inactivation compound (PIC), wherein the PIC is a psoralen, and wherein the platelet composition has a volume of about 250 mL to about 750 mL;
(b) photochemically inactivating the platelet composition in admixture with the PIC;
(c) transferring the resultant mixture of step (b) under sterile conditions to a container containing a compound adsorption device (CAD) to produce a pathogen-inactivated platelet composition;
wherein the CAD comprises at least about seven grams of adsorbent beads, and at least one of (i) and (ii) applies:
   (i) the volume of the container containing the CAD is about 1.2 to about 1.6 L; and
   (ii) the surface area of the interior of the container containing the CAD is about 800 $cm^2$ to about 1200 $cm^2$; and
(d) transferring the pathogen-inactivated platelet composition under sterile conditions from the container containing the CAD to three storage containers,
wherein the pathogen-inactivated platelet composition in each of said three storage containers is a therapeutic dosage unit of pathogen-inactivated platelets suitable for infusion.

29. The method of claim 28, wherein the platelet composition has a volume of about 250 mL to about 650 mL.

* * * * *